(12) United States Patent
Blander et al.

(10) Patent No.: US 9,314,484 B2
(45) Date of Patent: Apr. 19, 2016

(54) METHODS AND COMPOSITIONS FOR CANCER IMMUNOTHERAPY USING FLAGELLIN-TUMOR ASSOCIATED ANTIGEN FUSION PROTEIN EXPRESSING TUMOR CELLS

(71) Applicant: Icahn School of Medicine at Mount Sinai, New York, NY (US)

(72) Inventors: Julie Magarian Blander, North Haven, CT (US); Johan Garaude, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 14/484,374

(22) Filed: Sep. 12, 2014

(65) Prior Publication Data

US 2015/0064219 A1 Mar. 5, 2015

Related U.S. Application Data

(63) Continuation of application No. 13/577,295, filed as application No. PCT/US2011/023919 on Feb. 7, 2011, now abandoned.

(60) Provisional application No. 61/302,052, filed on Feb. 5, 2010, provisional application No. 61/306,618, filed on Feb. 22, 2010.

(51) Int. Cl.
*A61K 39/00* (2006.01)
*A61K 35/15* (2015.01)
*A61K 35/17* (2015.01)

(52) U.S. Cl.
CPC .................. *A61K 35/17* (2013.01); *A61K 35/15* (2013.01); *A61K 39/0011* (2013.01); *A61K 2039/5152* (2013.01); *A61K 2039/5154* (2013.01); *A61K 2039/5156* (2013.01); *A61K 2039/6068* (2013.01)

(58) Field of Classification Search
None
See application file for complete search history.

(56) References Cited

U.S. PATENT DOCUMENTS

| 6,130,082 | A | 10/2000 | Majarian et al. | |
| 8,324,369 | B2* | 12/2012 | Chen | 536/24.5 |
| 8,748,405 | B2* | 6/2014 | Yu et al. | 514/44 A |
| 2002/0061312 | A1* | 5/2002 | Medzhitov | 424/192.1 |
| 2003/0044429 | A1 | 3/2003 | Aderem et al. | |
| 2003/0175287 | A1* | 9/2003 | Medzhitov et al. | 424/185.1 |
| 2003/0232055 | A1* | 12/2003 | Medzhitov | 424/185.1 |
| 2008/0199485 | A1 | 8/2008 | Kundig et al. | |
| 2009/0087440 | A1 | 4/2009 | Vicari et al. | |
| 2009/0124557 | A1 | 5/2009 | Moyal-Amsellem et al. | |
| 2009/0220532 | A1 | 9/2009 | Leclerc et al. | |
| 2009/0297541 | A1 | 12/2009 | Ten Brinke et al. | |

FOREIGN PATENT DOCUMENTS

| WO | WO2006039701 | 4/2006 |
| WO | WO2009128949 | 3/2010 |

OTHER PUBLICATIONS

Xu et al., Tumor-specific dendritic cells generated by genetic redirection of Toll-like receptor signaling against the tumor-associated antigen, erbB2. Cancer Gene Ther. 14, 773-780, 2007.*
Kirk et al., Gene-modified dendritic cells for use in tumor vaccines, Human Gene Ther. 11, 797-806, 2000.*
Koido et al., Regulation of tumor immunity by tumor/dendritic cell fusions, Clin. Develop. Immunol. vol. 2010, art. ID. 516768, 2010.*
Garaude et al., "Flagellated" cancer cells propel anti-tumor immunity, *Oncolmmunology*, vol. 1, Issue 6, Sep. 2012, pp. 940-942.
Communication pursuant to Article 94(3) EPC for EP11740492.1 dated Oct. 7, 2014. 7 pages.
Xu et al. ,Tumor-specific dendritic cells generated by genetic redirection of Toll-like receptor signaling against the tumor-associated antigen, erbB2, Cancer Gene Ther. 14, 773-780, 2007.
International Search Report mailed Oct. 25, 2011, which issued in corresponding International Application No. PCT/US2011J023919.
Fearon et al.; "The Instructive Role of Innate Immunity in the Acquired Immune Response"; Science; vol. 272; pp. 50-53 (1996).
Medzhitov et al.; "Innate Immunity: The Virtues of a Nonclonal System of Recognition"; Cell; vol. 91; pp. 295-298 (1997).
Janeway et al.; "Approaching the Asymptote? Evolution and Revolution in Immunology"; Cold Spring Harb. Symp. Quant. Biol.; vol. 54; pp. 1-13 (1989).
Medzhitov et al.; "Innate immunity: impact on the adaptive immune response"; Curr. Opin Immunol.; vol. 94; pp. 4-9 (1997).
Strober et al.; "Signalling pathways and molecular interactions of NOD1 and NOD2"; Nat Rev Immunol.; vol. 6; No. 1; pp. 9-20 (2006).
Inohara et al.; "NOD-LRR Proteins: Role in Host-Microbial Interactions and Inflammatory Disease", Annu Rev Biochem.; vol. 74; pp. 355-383 (2005).
Chen G, Shaw MH, Kim YG, Nunez G.; "NOD-Like Receptors: Role in Innate Immunity and Inflammatory Disease"; Annu Rev Pathol.; vol. 4; pp. 365-398 (2009).
Martinon F, Mayor A, Tschopp; "The Inflammasomes: Guardians of the Body"; J. Annu Rev Immunol.; vol. 27; pp. 229-265 (2009).
Lemaitre et al.; "The Dorsoventral Regulatory Gene Cassette spatzlefToli/cactus Controls the Potent Antifungal Response in *Drosophila* Adults"; Cell; vol. 86; pp. 973-983 (1996).
Medzhitov et al.; "A human homologue of the *Drosophila* toll: protein signals activation of adaptive immunity"; Nature; vol. 388; pp. 394-397 (1997).
Rock et al.; "A family of human receptors structurally related to *Drosophila* toll"; Proc Natl Acad Sci USA; vol. 95; pp. 588-593 (1998).

(Continued)

*Primary Examiner* — Elly-Gerald Stoica
(74) *Attorney, Agent, or Firm* — Fish & Richardson P.C.

(57) ABSTRACT

Provided are methods for inducing an anti-tumor immune response by immunizing a mammal with a composition comprising a tumor cell which expresses a NLR ligand and/or TLR ligand-TAA fusion protein or with an activated DC which has internalized a tumor cell which expresses an NLR- and/or TLR ligand-TAA fusion protein.

15 Claims, 17 Drawing Sheets

(56) References Cited

OTHER PUBLICATIONS

Takeuchi et al.; "TLR6: A novel member of an expanding Toll-like receptor family"; Gene vol. 231; pp. 59-65 (1999).
Chuang and Ulevitch; "Identification of hTLR1 0: a novel human Toll-like receptor preferentially expressed in immune cells"; Biochim Biophys Acta_.; vol. 1518; pp. 157-161 (2001).
Schwandner et al.; "Peptidoglycan- and Lipoteichoic Acid-induced Cell Activation Is Mediated by Toll-like Receptor 2*"; J. Biol. Chem; vol. 274; pp. 17406-17409 (1999).
Hoshino et al.; "Cutting Edge: Toll-Like Receptor 4 (TLR4)-Deficient Mice Are Hyporesponsive to Lipopolysaccharide: Evidence for TLR4 as the Lps Gene Product"; J. Immunol; vol. 162; pp. 3749-3752 (1999).
Yoshimura et al.; "Cutting Edge: Recognition of Gram-Positive Bacterial Cell Wall Components by the Innate Immune System Occurs Via Toll-Like Receptor 2"; J. Immunol; vol. 163; pp. 1-5 (1999).
Aliprantis et al. ; "Cell Activation and Apoptosis by Bacterial Lipoproteins Through Toll-like Receptor-2"; Science; vol. 285; pp. 736-739 (1999).
Hemmi et al; "A Toll-like receptor recognizes bacterial DNA"; Nature; vol. 408; pp. 740-745 (2000).
Hayashi et al.; "The innate immune response to bacterial flagellin is mediated by Toll-like receptor 5"; Nature; vol. 410; pp. 1099-1103 (2001).
Alexopoulou et al.; "Recognition of double-stranded RNA and activation of NF-kB by Toll-like receptor 3"; Nature; vol. 413; pp. 732-738 (2001).
Underhill; "Macrophage recognition of zymosan particles"; J Endotoxin Res.; vol. 9; pp. 176-180 (2003).
Hornung V. et al.; "RNA Recognition via TLR7 and TLR 8"; Handb Exp Pharmacol; vol. 183; pp. 71-86 (2008).
Jurk M. et al.; "Human TLR7 or TLR8 independently confer responsiveness to the antiviral compound R-848"; Nat Immunol; vol. 3; pp. 499 (2002).
Franchi et al; "Cytosolic flagellin requires Ipaf for activation of caspase-1 and interleukin 1 beta in salmonella-infected macrophages"; Nat Immunol; vol. 7; No. 6; pp. 576-582 (2006).
Miao et al; Cytoplasmic flagellin activates caspase-1 and secretion of interleukin 1 beta via Iparf; Nat Immunol; vol. 7; No. 6; pp. 569-575 (2006).
Stephen, J.; "Anthrax Toxin"; Pharmacol. Ther; vol. 12; pp. 501-513 (1981).
Boyden et al.; "Nalp1b controls mouse macrophage susceptibility to anthrax lethal toxin"; Nat Genetics; vol. 38; pp. 240-244 (2006).
Lowy et al. "*Staphylococcus aureus* Infections", N. Engl. J. Med.; vol. 339; pp. 520-525 (1998).
Song et al.; "Structure of Staphylococcal alpha-Hemolysin, a Heptameric Transmembrane Pore"; Science; vol. 274; pp. 1859-1866 (1996).
Craven et al.; "*Staphylococcus aureus* alpha-Hemolysin Activates the NLRP3-lnflammasome in Human and Mouse Monocytic Cells"; PLoS One 4:e7446 (2009).
Munoz-Planillo et al.; "A Crytical Role for Hemolysins and Bacterial Lipoproteins in *Staphylococcus aureus* -Induced Activation of the Nlrp3 Inflammasome"; vol. 183; pp. 3942-3948 (2009).
Koski, G. K. et al., "Reengineering dendritic cell-based anti-cancer vaccines", Immunol Rev; vol. 222; pp. 256-276 (2008).
Herr, H. W. et al.; "Intravesical Bacillus Calmette-Guerin Therapy Presents Tumor Progression and Death From Superficial Bladder Cancer: Ten-Year Follow-Up of a Prospective Randomized Trial"; J Clin Oncol; vol. 13; No. 6; pp. 1404-1408 (1995).
Dougan, M. and Dranoff, G.; "Immune Therapy for Cancer"; Annu Rev Immunol; vol. 27; pp. 83-117 (2009).
Melief, C. J. et al.; "Effective therapeutic anticancer vaccines based on precision guiding of cytolytic T lymphocytes"; Immunol Rev; vol. 188; pp. 177-182 (2002).
Jackson, D. C. et al.; "A totally synthetic vaccine of generic structure that targets Toll-like receptor 2 on dendritic cells and promotes antibody or cytotoxic T cell responses"; Proc Natl Acad Sci USA; vol. 101; No. 43; pp. 15440 (2004).

Blander and Medzhitov; "Toll-dependent selection of microbial antigens for presentation by dendritic cells"; Nature; vol. 440, pp. 808 (2006).
Cote-Sierra et al.; "Bacterial Lipoprotein-Based Vaccines Induce Tumor Necrosis Factor-Dependent Type 1 Protective Immunity against Leishmania major"; Infect Immun; vol. 70; pp. 240-248 (2002).
Huleatt, J. W et al.; "Vaccination with recombinant fusion proteins incorporating Toll-like receptor ligands induces rapid cellular and humoral immunity"; Vaccine; vol. 25; pp. 763 (2007).
Huleatt, J. W. et al.; "Potent immunogenicity and efficacy of a universal influenza vaccine candidate comprising a recombinant fusion protein linking influenza M2e to the TLR5 ligand flagellin"; Vaccine; vol. 26; pp. 201 (2008).
Arimilli, S. et al., "Engineered Expression of the TLR5 Ligand Flagellin Enhances Paramyxovirus Activation of Human Dendritic Cell Function"; J Virol; vol. 82; No. 22; pp. 10975-10985 (2008).
Zitvogel L, et al.; "Therapy of murine tumors with tumor peptide-pulsed dendritic cells: dependence on T cells, B7 costimulation, and T helper cell I-associated cytokines"; J Exp Med; vol. 183; pp. 87-97 (1996).
Zhou LF, Tedder TF; "CD141 blood monocytes can differentiate into functionally mature CD831 dendritic cells"; Proc Natl Acad Sci USA; vol. 93; pp. 2588-2592 (1996).
Smith K D et al.; "Toll-like receptor 5 recognizes a conserved site on flagellin required for protofilament formation and bacterial motility"; Nat Immunol; vol. 4; No. 121 pp. 1247-1253 (2003).
Murthy K G et al.; "Identification of conserved domains in *Salmonella muenchen* flagellin that are essential for its ability to activate TLR5 and to induce an inflammatory response in vitro"; J Bioi Chem; vol. 279; ;No. 7; pp. 5667-5675 (2004).
Karla L Lightfield, et al.; "Critical function for Naip5 in inflammasome activation by a conserved carboxy-terminal domain of flagellin"; Nat Immunol; vol. 9; No. 10; pp. 1171-1178 (2008).
Robson NC, Hoves S, Maraskovsky E, Schnurr M; "Presentation of tumour antigens by dendritic cells and challenges faced", Curr Opin Immunol; vol. 22; No. 1; pp. 137-144 (2010).
Liangping Li; "Establishment of tumor cell lines by transient expression of immortalizing genes"; Gene Therapy and Molecular Biology; vol. 4; pp. 261-274 (1999).
Borrello I et al.; "A universal granulocyte-macrophage colony-stimulating factor-producing bystander cell line for use in the formulation of autologous tumor cell-based vaccines"; Hum Gene Ther; vol. 10; No. 12; pp. 1983-1991 (1999).
Gilliet, M. F. and F. O. Nestle; "Generation of Blood-Derived Human Dendritic Cells for Antitumor Immunotherapy"; Methods in Molecular Medicine; vol. 64; pp. 297-303 (2001).
Sallusto, F. and Lanzavecchia, A.; "Efficient Presentation of Soluble Antigen by Cultured Human Dendritic Cells is 1 Maintained by Granulocyte/Macrophage Colony-stimulating Factor Plus Interleukin 4 and Downregulated by Tumor Necrosis Factor alpha"; J. Exp. Med.; vol. 179; pp. 1109-1118 (1994).
Romani, N., et al.; "Proliferating Dendritic Cell Progenitors in human Blood"; J. Exp. Med ., vol. 180; pp. 83-93 (1994).
J.D. Wolchok, et al.; "Guidelines for the Evaluation of Immune Therapy Activity in Solid Tumors: Immune-Related Response Criteria"; Clinical Cancer Research; vol. 15; No. 23; pp. 7412-7420 (2009).
Ren et al.; "Flagellin-Deficient Legionella Mutants Evade Caspase-1- and Naip5-Mediated Macrophage Immunity"; PLoS Pathog; vol. 2; No. 3; pp. 18 (2006).
Tosch C et al.; "Adenovirus-mediatd gene transfer of pathogen-associated molecular patterns for cancer immunotherapy"; Cancer Gene Therapy; vol. 16; No. 4; pp. 310-319 (2009).
Cuadros C et al.; "Flagellin fusion proteins as adjuvants or vaccines induce specific immune responses"; Infection and Immunity, American Society for Macrobiology; vol. 72; No. 5; pp. 2810-2816 (2004).
Supplemental EP Search Report mailed Aug. 2, 2013, which issued in corresponding EP application No. EP11740492.

* cited by examiner

```
SEQUENCE LISTING

<160> NUMBER OF SEQ ID NOS: 32

<210> SEQ ID NO 1
<211> LENGTH: 293
<212> TYPE: PRT
<213> ORGANISM: Staphylococcus aureus

<400> SEQUENCE: 1

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gly
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gly Asn Trp Gly Pro Tyr Asp Arg Asp Ser Trp Asn Pro Val Tyr Gly
            180                 185                 190
```

```
Asn Gly Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
        210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 2
<211> LENGTH: 1826
<212> TYPE: DNA
<213> ORGANISM: Salmonella enterica subsp. enterica serovar Typhim

<400> SEQUENCE: 2
gttatcggca atctggaggc aaagtttaat gataattttg caaaataat gcgcggaata        60 atgatggata aagcggctat ttcgccgcct aagaaaaaga tcgggggaag tgaaaaattt      120
tctaaagttc gaaattcagg tgccgataca agggttacgg tgagaaaccg tggggaacag      180
cccaataaca tcaagttgta attgataagg aaaagatcat ggcacaagtc attaatacaa      240
acagcctgtc gctgttgacc cagaataacc tgaacaaatc ccagtccgct ctgggcaccg      300
ctatcgagcg tctgtcttcc ggtctgcgta tcaacagcgc gaaagacgat gcggcaggtc      360
aggcgattgc taaccgtttt accgcgaaca tcaaggtct gactcaggct tcccgtaacg       420
ctaacgaggg tatctccatt gcgcagacca ctgaaggcgc gctgaacgaa atcaacaaca      480
acctgcagcg tgtgcgtgaa ctggcggttc agtctgctaa cagcaccaac tcccagtctg      540
acctcgactc catccaggct gaaatcaccc agcgcctgaa cgaaatagac cgtgtatccg      600
gccagactca gttcaacggc gtgaaagtcc tggcgcagga caacaccctg accatccagg      660
ttggtgccaa cgacggtgaa actatcgata tcgatctgaa gcagatcaac tctcagaccc      720
tgggtctgga tacgctgaat gtgcaacaaa aatataaggt cagcgatacg gctgcaactg      780
ttacaggata tgccgatact acgattgctt tagacaatag tacttttaaa gcctcggcta      840
ctggtcttgg tggtactgac cagaaaattg atggcgattt aaaatttgat gatacgactg      900
gaaaatatta cgccaaagtt accgttacgg ggggaactgg taaagatggc tattatgaag      960
tttccgttga taagacgaac ggtgaggtga ctcttgctgg cggtgcgact tccccgctta     1020
caggtggact acctgcgaca gcaactgagg atgtgaaaaa tgtacaagtt gcaaatgctg     1080
atttgacaga ggctaaagcc gcattgacag cagcaggtgt taccggcaca gcatctgttg     1140
ttaagatgtc ttatactgat aataacggta aaactattga tggtggttta gcagttaagg     1200
taggcgatga ttactattct gcaactcaaa ataaagatgg ttccataagt attaatacaa     1260
cgaaatacac tgcagatgac ggtacatcca aaactgcact aaacaaactg ggtggcgcag     1320
acggcaaaac cgaagttgtt tctattggtg gtaaaactta cgctgcaagt aaagccgaag     1380
gtcacaactt taaagcacag cctgatctgg cggaagcggc tgctacaacc accgaaaacc     1440
cgctgcagaa aattgatgct gctttggcac aggttgacac gttacgttct gacctgggtg     1500
```

-continued

```
cggtacagaa ccgtttcaac tccgctatta ccaacctggg caacaccgta acaacctga      1560 cttctgcccg tagccgtatc gaagattccg actacgcgac cgaagtttcc aacatgtctc    1620
gcgcgcagat tctgcagcag gccggtacct ccgttctggc gcaggcgaac caggttccgc    1680
aaaacgtcct ctctttactg cgttaatgcg ttaatccggc gattgattca ccgacacgtg    1740
gtacacaatc aatggcagcg aaagctgcct tttttaaccg cgcacgccct atgtaatgaa    1800
agaaatcacc gtacctgaac ctgcct                                          1826
```

<210> SEQ ID NO 3
<211> LENGTH: 132
<212> TYPE: PRT
<213> ORGANISM: PSEUDOMONAS SYRINGAE PV. PHASEOLICOLA

<400> SEQUENCE: 3

```
Met Val Met Asp Met Ser Val Lys Leu Asn Val Ser Tyr Pro Ala Ala
1               5                   10                  15

Gln Pro Ala Ser Gln Val Pro Val Pro Asp Lys Ser Val Asp Lys Pro
            20                  25                  30

Ala Asp Thr Pro Ser Val Glu Arg Val Ala Ala Thr Ala Glu Ser Lys
        35                  40                  45

Gly Ser Asp Leu His Lys Asp Ser His Asp Glu Ala Lys Val Lys
    50                  55                  60

Ala Ala Ala Glu Asp Ile Gly Lys Phe Phe His Ser Val Lys Arg Asn
65                  70                  75                  80

Leu Glu Phe Ser Ile Asp Glu Ala Ser Gly Lys Val Ile Val Lys Val
                85                  90                  95

Ile Ala Ser Asp Ser Gly Glu Val Val Arg Gln Ile Pro Asn Ala Glu
            100                 105                 110

Ile Leu Lys Leu Ala Asp Ser Leu Ser Asp Ala Asn Ser Leu Leu Phe
        115                 120                 125

Arg Ala Lys Ala
    130
```

<210> SEQ ID NO 4
<211> LENGTH: 282
<212> TYPE: PRT
<213> ORGANISM: PSEUDOMONAS SYRINGAE PV. PHASEOLICOLA

<400> SEQUENCE: 4

```
Met Ala Leu Thr Val Asn Thr Asn Val Ala Ser Leu Asn Val Gln Lys
1               5                   10                  15

Asn Leu Gly Arg Ala Ser Asp Ala Leu Ser Thr Ser Met Thr Arg Leu
            20                  25                  30

Ser Ser Gly Leu Lys Ile Asn Ser Ala Lys Asp Asp Ala Ala Gly Leu
        35                  40                  45

Gln Ile Ala Thr Lys Ile Thr Ser Gln Ile Arg Gly Gln Thr Met Ala
    50                  55                  60

Ile Lys Asn Ala Asn Asp Gly Met Ser Leu Ala Gln Thr Ala Glu Gly
65                  70                  75                  80

Ala Leu Gln Glu Ser Thr Asn Ile Leu Gln Arg Met Arg Glu Leu Ala
                85                  90                  95

Val Gly Ser Arg Asn Asp Ser Asn Ser Ser Thr Asp Arg Asp Ala Leu
            100                 105                 110

Asn Lys Glu Phe Thr Ala Met Ser Ser Glu Leu Thr Arg Ile Ala Gln
        115                 120                 125
```

```
Ser Thr Asn Leu Asn Gly Lys Asn Leu Leu Asp Gly Ser Ala Ser Thr
    130                 135                 140

Met Thr Phe Gln Val Gly Ser Asn Ser Gly Ala Ser Asn Gln Ile Thr
145                 150                 155                 160

Leu Thr Leu Ser Ala Ser Phe Asp Ala Asn Thr Leu Gly Val Gly Ser
                165                 170                 175

Ala Val Thr Ile Ala Gly Ser Asp Ser Thr Thr Ala Glu Thr Asn Phe
            180                 185                 190

Ser Ala Ala Ile Ala Ala Ile Asp Ser Ala Leu Gln Thr Ile Asn Ser
        195                 200                 205

Thr Arg Ala Asp Leu Gly Ala Ala Gln Asn Arg Leu Thr Ser Thr Ile
    210                 215                 220

Ser Asn Leu Gln Asn Ile Asn Glu Asn Ala Ser Ala Ala Leu Gly Arg
225                 230                 235                 240

Val Gln Asp Thr Asp Phe Ala Ala Glu Thr Ala Gln Leu Thr Lys Gln
                245                 250                 255

Gln Thr Leu Gln Gln Ala Ser Thr Ser Val Leu Ala Gln Ala Asn Gln
            260                 265                 270

Leu Pro Ser Ala Val Leu Lys Leu Leu Gln
        275                 280

<210> SEQ ID NO 5
<211> LENGTH: 266
<212> TYPE: PRT
<213> ORGANISM: BACILLUS CEREUS

<400> SEQUENCE: 5

Met Arg Ile Gly Thr Asn Val Leu Ser Met Asn Ala Arg Gln Ser Leu
1               5                   10                  15

Tyr Glu Asn Glu Lys Arg Met Asn Val Ala Met Glu His Leu Ala Thr
            20                  25                  30

Gly Lys Lys Leu Asn His Ala Ser Asn Asn Pro Ala Asn Ile Ala Ile
        35                  40                  45

Val Thr Arg Met His Ala Arg Ala Ser Gly Met Arg Val Ala Ile Arg
    50                  55                  60

Asn Asn Glu Asp Ala Leu Ser Met Leu Arg Thr Ala Glu Ala Ala Leu
65                  70                  75                  80

Gln Thr Val Thr Asn Ile Leu Gln Arg Met Arg Asp Leu Ala Val Gln
                85                  90                  95

Ser Ala Asn Val Thr Asn Ser Asn Lys Asn Arg Asn Ser Leu Asn Lys
            100                 105                 110

Glu Phe Gln Ser Leu Thr Glu Gln Ile Ser Tyr Ile Gly Glu Thr Thr
        115                 120                 125

Glu Phe Asn Asp Leu Ser Val Phe Asp Gly Gly Asn Arg Pro Val Thr
    130                 135                 140

Leu Asp Asp Ile Gly Tyr Thr Val Asn Val Thr Lys His Thr Pro Pro
145                 150                 155                 160

Ser Pro Thr Gln His Asp Ile Lys Ile Ser Thr Glu Gln Glu Ala Arg
                165                 170                 175

Ala Ala Ile Arg Lys Ile Glu Glu Ala Leu Gln Asn Val Ser Leu His
            180                 185                 190

Arg Ala Asp Leu Gly Ser Met Met Asn Arg Leu Gln Phe Asn Ile Glu
        195                 200                 205

Asn Leu Asn Ser Gln Ser Met Ala Leu Thr Asp Ala Ala Ser Arg Ile
    210                 215                 220
```

```
Glu Asp Ala Asp Met Ala Gln Glu Met Ser Asp Phe Leu Lys Phe Lys
225                 230                 235                 240

Leu Leu Thr Glu Val Ala Leu Ser Met Val Ser Gln Ala Asn Gln Ile
                245                 250                 255

Pro Gln Met Val Ser Lys Leu Leu Gln Ser
            260                 265

<210> SEQ ID NO 6
<211> LENGTH: 460
<212> TYPE: PRT
<213> ORGANISM: BACILLUS CEREUS

<400> SEQUENCE: 6

Met Arg Ile Asn Thr Asn Ile Asn Ser Met Arg Thr Gln Glu Tyr Met
1               5                   10                  15

Arg Gln Asn Gln Ala Lys Met Ser Thr Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Met Ile Arg Ala Arg Glu Ser Gly Leu Gly Val Ala Ala Asn
    50                  55                  60

Asn Thr Gln Asp Gly Ile Ser Leu Ile Arg Thr Ala Asp Ser Ala Met
65                  70                  75                  80

Asn Ser Val Ser Asn Ile Leu Leu Arg Met Arg Asp Leu Ala Asn Gln
                85                  90                  95

Ser Ala Asn Gly Thr Asn Thr Asp Lys Asn Gln Gly Ala Leu Asp Lys
            100                 105                 110

Glu Phe Ala Ala Leu Lys Glu Gln Ile Asp Tyr Ile Ser Lys Asn Thr
        115                 120                 125

Glu Phe Asn Asp Lys Lys Leu Leu Asp Gly Ser Asn Lys Ala Ile Ala
    130                 135                 140

Ile Gln Thr Leu Asp Ser Asp Asp Lys Gly Lys Gln Ile Asp Ile Ser
145                 150                 155                 160

Leu Ser Asp Thr Ser Thr Thr Ala Leu Lys Ile Asn Asn Leu Ser Ile
                165                 170                 175

Ala Ala Asn Gly Leu Gly Ile Gly Ser Gly Lys Glu Leu Tyr Gly Val
            180                 185                 190

Ala Asp Asn Thr Ile Ala Asn Ala Ser Ala Glu Ala Leu Lys Lys Leu
        195                 200                 205

Asp Gly Thr Thr Gly Asp Thr Asp Val Lys Arg Ser Asn Ala Val Lys
    210                 215                 220

Ala Phe Thr Asp Gly Tyr Lys Asp Leu Lys Val Ala Met Asn Ala Lys
225                 230                 235                 240

Asp Val Glu Thr Ile Asp Ala Ala Ile Lys Lys Phe Glu Gly Ala Asn
                245                 250                 255

Thr Leu Glu Asn Ala Gln Ala Ile Gly Ala Ala Phe Glu Gly Ala Ala
            260                 265                 270

Lys Ala Thr Leu Thr Thr Asp Ile Asn Asn Ala Thr Leu Thr Ser Lys
        275                 280                 285

Ala Leu Ser Asp Leu Asp Thr Asp Ser Thr Thr Glu Thr Arg Lys Ala
    290                 295                 300

Ala Met Lys Asp Phe Val Ala Ala Phe Asp Lys Val Lys Gly Ser Met
305                 310                 315                 320

Asn Ser Ser Asp Val Thr Lys Ile Ser Asp Ala Ile Asp Arg Phe Ser
```

```
                325                 330                 335
Lys Thr Asp Asp Ser Gly Asn Thr Leu Glu Ala Ala Arg Ala Ile Gly
            340                 345                 350

Asp Ala Phe Lys Ala Ala Thr Thr Asn Gly Lys Thr Ser Thr Ala Thr
        355                 360                 365

Asp Ala Asn Ser Ala Ile Lys Ala Ile Asp Glu Ala Leu Glu Thr Ile
    370                 375                 380

Ala Ser Asn Arg Ala Thr Leu Gly Ala Thr Leu Asn Arg Leu Asp Phe
385                 390                 395                 400

Asn Val Asn Asn Ile Lys Asn Gly Ala Ser Ser Met Ala Ser Ala Ala
                405                 410                 415

Ser Gln Val Glu Asp Ala Asp Met Ala Lys Glu Met Ser Glu Met Thr
            420                 425                 430

Lys Phe Lys Ile Leu Asn Glu Ala Gly Ile Ser Met Leu Ser Gln Ala
        435                 440                 445

Asn Gln Thr Pro Gln Met Val Ser Lys Leu Leu Gln
    450                 455                 460

<210> SEQ ID NO 7
<211> LENGTH: 116
<212> TYPE: PRT
<213> ORGANISM: Bacillus thuringiensis serovar israelensis

<400> SEQUENCE: 7

Met Thr Pro Trp Ala Arg Ile Thr Ile Asn Leu Glu Ile Asp Phe Phe
1               5                   10                  15

Ala Tyr Tyr Arg Phe Ser Ile Cys Arg Lys Val Asn Ile Lys Lys Trp
            20                  25                  30

Gly Phe Leu Asn Met Arg Ile Asn Thr Asn Ile Asn Ser Met Arg Thr
        35                  40                  45

Gln Glu Tyr Met Arg Gly Asn Gln Ala Lys Met Asn Ala Met Asp Arg
    50                  55                  60

Leu Ser Ser Gly Lys Arg Ile Asn Ser Ala Ser Asp Asp Ala Ala Gly
65                  70                  75                  80

Leu Ala Ile Ala Thr Arg Met Lys Ala Arg Glu Gly Gly Leu Asn Val
                85                  90                  95

Ala Gly Met Thr Gln Asp Gly Met Ser Leu Ile Arg Thr Leu Asp Ser
            100                 105                 110

Pro Tyr Ser Glu
        115

<210> SEQ ID NO 8
<211> LENGTH: 118
<212> TYPE: PRT
<213> ORGANISM: Bacillus thuringiensis serovar israelensis

<400> SEQUENCE: 8

Met Thr Pro Val Val Ala Arg Ile Thr Ile Asn Leu Glu Ile Asp Phe
1               5                   10                  15

Phe Ala Tyr Tyr Arg Phe Ser Ile Cys Arg Lys Val Asn Ile Lys Lys
            20                  25                  30

Trp Gly Phe Leu Asn Met Arg Ile Asn Thr Asn Ile Asn Ser Met Arg
        35                  40                  45

Thr Gln Glu Tyr Met Arg Gln Asn Gln Ala Lys Met Ser Asn Ala Met
    50                  55                  60

Asp Arg Leu Ser Ser Gly Lys Arg Ile Asn Ser Ala Ser Asp Asp Ala
```

```
            65                  70                  75                  80
Ala Gly Leu Ala Ile Ala Thr Arg Met Lys Ala Arg Glu Gly Gly Leu
                    85                  90                  95

Asn Val Ala Gly Met Thr Gly Asp Gly Met Ser Leu Ile Arg Thr Leu
                100                 105                 110

Asp Ser Pro Tyr Ser Glu
            115

<210> SEQ ID NO 9
<211> LENGTH: 606
<212> TYPE: PRT
<213> ORGANISM: THIOBACILLUS DENITRIFICANS

<400> SEQUENCE: 9

Met Ala Ala Val Ile Asn Thr Asn Ile Ala Ser Leu Asn Ala Gly Met
1               5                   10                  15

Ile Asn Ser Ser Gln Ala Ser Leu Ala Thr Ser Leu Gln Arg Leu Ser
            20                  25                  30

Ser Gly Leu Arg Ile Asn Ser Ala Lys Asp Asp Ala Ala Gly Leu Ala
        35                  40                  45

Ile Ser Asp Arg Phe Thr Thr Gln Ile Arg Gly Ile Asn Gly Ala Ala
    50                  55                  60

Met Ala Asn Asp Gly Ile Ser Leu Ala Gln Thr Ala Glu Gly Ala Leu
65                  70                  75                  80

Thr Glu Thr Gly Ala Asn Leu Gln Arg Ile Arg Glu Leu Ala Val Gln
                85                  90                  95

Ser Ala Asn Ser Thr Asn Ser Ala Ser Asp Arg Lys Ala Leu Asn Ala
            100                 105                 110

Glu Val Gln Gln Leu Leu Ala Glu Val Gln Arg Val Gly Thr Thr Thr
        115                 120                 125

Glu Phe Asn Gly Leu Lys Leu Leu Asp Gly Thr Phe Ser Asn Ala Gln
    130                 135                 140

Phe Gln Val Gly Ala Asn Ala Asn Gln Thr Ile Ser Val Thr Val Ser
145                 150                 155                 160

Gly Ala Thr Thr Asp Leu Ile Gly Ala Tyr Gln Ala Thr Gly Asn Ala
                165                 170                 175

Val Thr Ser Ala Ala Phe Asp Gly Ser Gly Phe Thr Ile Asn Gly Val
            180                 185                 190

Glu Ile Gly Val Ser Ala Gly Thr Ser Ala Ala Gly Val Thr Ala Asp
        195                 200                 205

Ser Ala Thr Ala Lys Ala Thr Ala Ile Asn Ala Lys Thr Gly Glu Thr
    210                 215                 220

Gly Val Thr Ala Thr Ala Ser Ser Asn Val Thr Gly Ser Gly Pro Thr
225                 230                 235                 240

Ala Arg Ser Gly Leu Ala Ser Gly Ala Leu Leu Ile Asn Gly Ile Ala
                245                 250                 255

Val Gly Ala Ile Ala Ala Asp Thr Asn Ala Val Thr Gly Gly Met Ala
            260                 265                 270

Ala Thr Ala Ile Asn Ala Val Ser Asn Gln Thr Gly Val Ser Ala Val
        275                 280                 285

Ala Asp Ala Thr Thr Gly Ala Leu Thr Leu Ser Thr Ala Asp Gly Arg
    290                 295                 300

Asn Ile Glu Leu Thr Ser Ser Pro Ala Thr Ala Ala Gly Ala Gln Ala
305                 310                 315                 320
```

```
Ile Gln Asn Ala Thr Gly Leu Asp Val Ser Ala Gly Ser Asn Ala Ser
                325                 330                 335

Gly Asn Glu Thr Ala Thr Leu Thr Phe Ala Val Ala Asn Ala Asn Ala
            340                 345                 350

Ala Gly Gly Ile Thr Thr Ala Asn Gly Gly Asp Thr Ile Thr Ile
        355                 360                 365

Gly Glu Arg Thr Tyr Gly Phe Thr Ile Asp Gly Val Ala Ala Gly
    370                 375                 380

Asn Val Ala Val Thr Leu Ala Ala Gly Ala Glu Thr Val Ala Ile
385                 390                 395                 400

Ala Asn Ile Lys Thr Ala Ile Asn Ala Glu Tyr Ala Ala Gly Arg Thr
                405                 410                 415

Ala Val Gln Gly Gly Ala Thr Thr Ala Thr Ser Leu Val Val Thr Ser
                420                 425                 430

Ser Lys Leu Gly Thr Gly Thr Leu Ala Ile Ala Glu Thr Ala Thr Asn
                435                 440                 445

Ala Ala Ala Ile Ala Pro Gly Ala Ser Gly Gly Thr Ala Ala Ala
            450                 455                 460

Asp Gly Ser Gly Met Thr Thr Arg Gly Thr Leu Thr Leu Ser Ser Pro
465                 470                 475                 480

Glu Ser Phe Thr Val Ala Gly Ala Asp Val Ala Tyr Gly Leu Gly
            485                 490                 495

Ser Val Ser Ala Ser Leu Thr Lys Leu Asn Thr Val Asp Ile Ser Thr
                500                 505                 510

Val Ala Gly Ser Asn Ala Ala Leu Ala Val Leu Asp Gly Ala Leu Ser
                515                 520                 525

Gln Val Thr Ser Gln Arg Ala Thr Leu Gly Ala Val Gln Asn Arg Phe
                530                 535                 540

Ala Ser Thr Val Ser Asn Leu Gln Thr Thr Ala Glu Asn Leu Ser Ala
545                 550                 555                 560

Ala Arg Ser Arg Ile Val Asp Ala Asp Phe Ala Ala Glu Thr Ala Asn
                565                 570                 575

Leu Thr Arg Gly Gln Ile Leu Gln Gln Ala Gly Thr Ala Met Leu Ala
                580                 585                 590

Gly Ala Asn Gly Leu Pro Asn Gln Val Leu Ser Leu Leu Arg
            595                 600                 605

<210> SEQ ID NO 10
<211> LENGTH: 160
<212> TYPE: PRT
<213> ORGANISM: Borrelia lusitaniae

<400> SEQUENCE: 10

Glu Gln Leu Thr Asp Glu Ile Asn Arg Ile Ala Asp Gln Ala Gln Tyr
1               5                   10                  15

Asn Gln Met His Met Leu Ser Asn Lys Ser Ala Ser Gln Asn Val Arg
                20                  25                  30

Thr Ala Glu Glu Leu Gly Met Gln Pro Ala Lys Ile Asn Thr Pro Ala
            35                  40                  45

Ser Leu Ser Gly Ser Gln Ala Ser Trp Thr Leu Arg Val His Val Gly
        50                  55                  60

Ala Asn Gln Asp Glu Ala Ile Ala Val Asn Ile Tyr Ala Ala Asn Val
65                  70                  75                  80

Ala Asn Leu Phe Ser Gly Glu Gly Ala Gln Val Ala Gln Ala Ala Pro
                85                  90                  95
```

```
Ala Gln Glu Gly Val Gln Glu Gly Ala Gln Pro Ala
            100                 105                 110

Thr Ala Pro Ser Gln Gly Gly Val Asn Ser Pro Ile Asn Val Thr Thr
            115                 120                 125

Thr Val Asp Ala Asn Thr Ser Leu Ala Lys Ile Glu Asn Ala Ile Arg
        130                 135                 140

Met Val Ser Asp Gln Arg Ala Asn Leu Gly Ala Phe Gln Asn Arg Leu
145                 150                 155                 160

<210> SEQ ID NO 11
<211> LENGTH: 160
<212> TYPE: PRT
<213> ORGANISM: Borrelia valaisiana

<400> SEQUENCE: 11

Glu Gln Leu Thr Asp Glu Ile Asn Arg Ile Ala Asp Gln Ala Gln Tyr
1               5                   10                  15

Asn Gln Met His Met Leu Ser Asn Lys Ser Ala Ala Gln Asn Val Lys
            20                  25                  30

Thr Ala Glu Glu Leu Gly Met Gln Pro Ala Lys Ile Asn Thr Pro Ala
        35                  40                  45

Ser Leu Ser Gly Ser Gln Ala Ser Trp Thr Leu Arg Val His Val Gly
    50                  55                  60

Ala Asn Gln Asp Glu Ala Ile Ala Val Asn Ile Tyr Ala Ala Asn Val
65                  70                  75                  80

Ala Asn Leu Phe Ser Gly Glu Gly Ala Gln Thr Ala Gln Ala Thr Pro
                85                  90                  95

Val Gln Glu Gly Ala Gln Gln Glu Gly Ala Gln Gln Pro Ala Pro Ala
            100                 105                 110

Thr Ala Pro Ser Gln Gly Gly Val Asn Ser Pro Val Asn Val Thr Thr
            115                 120                 125

Thr Val Asp Ala Asn Thr Ser Leu Ala Lys Ile Glu Asn Ala Ile Arg
        130                 135                 140

Met Ile Ser Asp Gln Arg Ala Asn Leu Gly Ala Phe Gln Asn Arg Leu
145                 150                 155                 160

<210> SEQ ID NO 12
<211> LENGTH: 160
<212> TYPE: PRT
<213> ORGANISM: Borrelia garinli

<400> SEQUENCE: 12

Glu Gln Leu Thr Asp Glu Ile Asn Arg Ile Ala Asp Gln Ala Gln Tyr
1               5                   10                  15

Asn Gln Met His Met Leu Ser Asn Lys Ser Ala Ser Gln Asn Val Arg
            20                  25                  30

Thr Ala Glu Glu Leu Gly Met Gln Pro Ala Lys Ile Asn Thr Pro Ala
        35                  40                  45

Ser Leu Ser Gly Ser Gln Ala Ser Trp Thr Leu Arg Val His Val Gly
    50                  55                  60

Ala Asn Gln Asp Glu Ala Ile Ala Val Asn Ile Tyr Ala Ala Asn Val
65                  70                  75                  80

Ala Asn Leu Phe Ser Gly Glu Gly Ala Gln Ala Ala Gln Thr Ala Pro
                85                  90                  95

Val Gln Glu Gly Val Gln Gln Glu Gly Ala Gln Gln Pro Ala Pro Ala
            100                 105                 110
```

```
Thr Ala Pro Ser Gln Gly Gly Val Asn Ser Pro Val Asn Val Thr Thr
        115                 120                 125

Thr Val Asp Ala Asn Thr Ser Leu Ala Lys Ile Glu Asn Ala Ile Arg
    130                 135                 140

Met Ile Ser Asp Gln Arg Ala Asn Leu Gly Ala Phe Gln Asn Arg Leu
145                 150                 155                 160

<210> SEQ ID NO 13
<211> LENGTH: 160
<212> TYPE: PRT
<213> ORGANISM: Borrelia afzelii

<400> SEQUENCE: 13

Glu Gln Leu Thr Asp Glu Ile Asn Arg Ile Ala Asp Gln Ala Gln Tyr
1               5                   10                  15

Asn Gln Met His Met Ile Ser Asn Lys Ser Ala Ser Gly Asn Val Lys
            20                  25                  30

Thr Ala Glu Glu Leu Gly Met Gln Pro Ala Lys Ile Asn Thr Pro Ala
        35                  40                  45

Ser Leu Ser Gly Ser Gln Ala Ser Trp Thr Leu Arg Val His Val Gly
    50                  55                  60

Ala Asn Gln Asp Glu Ala Ile Ala Val Asn Ile Tyr Ser Ala Asn Val
65                  70                  75                  80

Ala Asn Leu Phe Ser Gly Glu Gly Ala Gln Ala Ala Gln Ala Ala Pro
                85                  90                  95

Val Gln Glu Gly Ala Gln Glu Gly Ala Gln Gln Pro Thr Pro Ala
            100                 105                 110

Thr Ala Pro Thr Gln Gly Gly Val Asn Ser Pro Val Asn Val Thr Thr
        115                 120                 125

Thr Val Asp Ala Asn Thr Ser Leu Ala Lys Ile Glu Asn Ala Ile Arg
    130                 135                 140

Met Ile Ser Asp Gln Arg Ala Asn Leu Gly Ala Phe Gln Asn Arg Leu
145                 150                 155                 160

<210> SEQ ID NO 14
<211> LENGTH: 160
<212> TYPE: PRT
<213> ORGANISM: Borrelia burgdorferi

<400> SEQUENCE: 14

Glu Gln Leu Thr Asp Glu Ile Asn Arg Ile Ala Asp Gln Ala Gln Tyr
1               5                   10                  15

Asn Gln Met His Met Leu Ser Asn Lys Ser Ala Ser Gln Asn Val Arg
            20                  25                  30

Thr Ala Glu Glu Leu Gly Met Gln Pro Ala Lys Ile Asn Thr Pro Ala
        35                  40                  45

Ser Leu Ser Gly Ser Gln Ala Ser Trp Thr Leu Arg Val His Val Gly
    50                  55                  60

Ala Asn Gly Asp Glu Ala Ile Ala Val Asn Ile Tyr Ala Ala Asn Val
65                  70                  75                  80

Ala Asn Leu Phe Ser Gly Glu Gly Ala Gln Thr Ala Gln Ala Ala Pro
                85                  90                  95

Val Gln Glu Gly Val Gln Gln Glu Gly Ala Gln Gln Pro Ala Pro Ala
            100                 105                 110

Thr Ala Pro Ser Gln Gly Gly Val Asn Ser Pro Val Asn Val Thr Thr
        115                 120                 125
```

```
Thr Tyr Asp Ala Asn Thr Ser Leu Ala Lys Ile Glu Asn Ala Ile Arg
            130                 135                 140

Met Ile Ser Asp Gln Arg Ala Asn Leu Gly Ala Phe Gln Asn Arg Leu
145                 150                 155                 160

<210> SEQ ID NO 15
<211> LENGTH: 130
<212> TYPE: PRT
<213> ORGANISM: PSEUDOMONAS SYRINGAE PV. PIIASEOLICOLA

<400> SEQUENCE: 15

Met Val Met Asp Met Ser Val Lys Leu Asn Val Ser Tyr Pro Ala Ala
1               5                   10                  15

Gln Pro Ala Ser Gln Val Pro Val Pro Asp Lys Ser Val Asp Lys Pro
            20                  25                  30

Ala Asp Thr Pro Ser Val Glu Arg Val Ala Thr Ala Glu Ser Lys
        35                  40                  45

Gly Ser Asp Leu His Lys Asp Ser His Asp Glu Ala Lys Val Lys
    50                  55                  60

Ala Ala Ala Glu Asp Ile Gly Lys Phe Leu His Ser Val Lys Met Leu
65                  70                  75                  80

Glu Phe Ser Ile Asp Glu Ala Ser Gly Lys Val Ile Val Lys Val Ile
                85                  90                  95

Ala Ser Asp Ser Gly Glu Trp Arg Gly Ile Pro Asn Ala Glu Ile Leu
            100                 105                 110

Lys Leu Ala Asp Ser Leu Ser Asp Ala Asn Ser Leu Leu Phe Arg Ala
        115                 120                 125

Lys Ala
    130

<210> SEQ ID NO 16
<211> LENGTH: 282
<212> TYPE: PRT
<213> ORGANISM: Pseudomonas syringae pv. phaseolicola

<400> SEQUENCE: 16

Met Ala Leu Thr Val Asn Thr Asn Val Ala Ser Leu Asn Val Gln Lys
1               5                   10                  15

Asn Leu Gly Arg Ala Ser Asp Ala Leu Ser Thr Ser Met Thr Arg Leu
            20                  25                  30

Ser Ser Gly Leu Lys Ile Asn Ser Ala Lys Asp Asp Ala Ala Gly Leu
        35                  40                  45

Gln Ile Ala Thr Lys Ile Thr Ser Gln Ile Arg Gly Gln Thr Met Ala
    50                  55                  60

Ile Lys Asn Ala Asn Asp Gly Met Ser Leu Ala Gln Thr Ala Glu Gly
65                  70                  75                  80

Ala Leu Gln Glu Ser Thr Asn Ile Leu Gln Arg Met Arg Glu Leu Ala
                85                  90                  95

Val Gly Ser Arg Asn Asp Ser Asn Ser Ser Thr Asp Arg Asp Ala Leu
            100                 105                 110

Asn Lys Glu Phe Thr Ala Met Ser Ser Glu Leu Thr Arg Ile Ala Gln
        115                 120                 125

Ser Thr Asn Ile Asn Gly Lys Asn Leu Leu Asp Gly Ser Ala Ser Thr
    130                 135                 140

Met Thr Phe Gly Val Gly Ser Asn Ser Gly Ala Ser Asn Gln Ile Thr
145                 150                 155                 160
```

```
Leu Thr Leu Ser Ala Ser Phe Asp Ala Asn Thr Leu Gly Val Gly Ser
            165                 170                 175

Ala Val Thr Ile Ala Gly Ser Asp Ser Thr Thr Ala Glu Thr Asn Phe
            180                 185                 190

Ser Ala Ala Ile Ala Ala Ile Asp Ser Ala Leu Gln Thr Ile Asn Ser
            195                 200                 205

Thr Arg Ala Asp Leu Gly Ala Ala Gln Asn Arg Leu Thr Ser Thr Ile
            210                 215                 220

Ser Asn Leu Gln Asn Ile Asn Glu Asn Ala Ser Ala Ala Leu Gly Arg
225                 230                 235                 240

Val Gln Asp Thr Asp Phe Ala Ala Glu Thr Ala Gln Leu Thr Lys Gln
            245                 250                 255

Gln Thr Leu Gln Gln Ala Ser Thr Ser Val Leu Ala Gln Ala Asn Gly
            260                 265                 270

Leu Pro Ser Ala Val Leu Lys Leu Leu Gln
            275                 280
```

<210> SEQ ID NO 17
<211> LENGTH: 99
<212> TYPE: PRT
<213> ORGANISM: Borrelia sp.

<400> SEQUENCE: 17

```
Ala Ser Leu Ser Gly Ser Gly Ala Ser Trp Thr Leu Arg Val His Val
1               5                   10                  15

Gly Ala Asn Gln Asp Glu Ala Ile Ala Val Asn Ile Tyr Ala Ala Asn
            20                  25                  30

Val Ala Asn Leu Phe Ser Gly Glu Gly Ala Gln Gln Val Ala Pro Ala
            35                  40                  45

Gln Glu Gly Ala Gln Gln Gly Ala Gln Ala Ala Pro Ala Pro Ala
            50                  55                  60

Ala Ala Pro Ala Gln Gly Gly Val Asn Ser Pro Val Asn Val Thr Thr
65                  70                  75                  80

Ala Val Asp Ala Asn Met Ser Leu Thr Lys Ile Glu Asp Ala Ile Arg
                85                  90                  95

Met Ile Thr
```

<210> SEQ ID NO 18
<211> LENGTH: 334
<212> TYPE: PRT
<213> ORGANISM: Wigglesworthia glossinidia

<400> SEQUENCE: 18

```
Gly Ala Ile Asn Glu Ile Asn Glu Asn Met His Ala Ile Arg Arg Leu
1               5                   10                  15

Thr Val Gln Ile Lys Ser Thr Ala Ser Val Ser Lys Ala Asp Lys Lys
            20                  25                  30

Ser Ile Gln Asp Glu Ile Lys Lys Arg Leu Ser Glu Ile Asp Arg Leu
            35                  40                  45

Ala Glu Gly Thr Glu Ser Asn Gly Met Lys Ile Leu Ser Gly Asn Gly
            50                  55                  60

Arg Leu Ser Val Gly Ile Gly Ala Asn Asp Gly Gln Val Val Asn Ile
65                  70                  75                  80

Asp Leu Phe Lys Leu Asp Thr Glu Ser Leu His Val Lys Asp Phe Asn
                85                  90                  95
```

```
Val Asn Ser Asp Ala Leu Tyr Ala Ser Asp Ile Asp Glu Asn Ala Val
                100                 105                 110

Thr Ser Ala Lys Ile Gly Ile Glu Ala Lys Lys Ile Leu Asp Ser Ser
            115                 120                 125

Thr Pro Glu Ser Lys Lys Asn Ile Lys Arg Gly Leu Tyr Glu Ser Gly
        130                 135                 140

Gly Glu Tyr Phe Phe Lys Gln Ile Asp Gly Asn Glu Tyr Tyr Lys Val
145                 150                 155                 160

Glu Ile Ser Asn Thr Gly Val Ala Gly Tyr Asn Ser Ser Pro Ala
                165                 170                 175

Glu Leu Thr Glu Ile Pro Lys Ser Val Lys Thr Ala Gln Ile Thr Val
                180                 185                 190

Glu Ile Asp Pro Lys Thr Leu Ala Val Gly Glu Thr Leu Lys Ser Tyr
            195                 200                 205

Met Lys Asp Gly Ile Gln Gln Tyr Leu Ile His Lys Gln Glu Gly Asp
        210                 215                 220

Lys Glu Ile Tyr His Glu Ala Ile Ile Asn Tyr Glu Gly Lys Val Lys
225                 230                 235                 240

Ser Gly Ser Glu Leu Asp Phe Glu Thr Leu Leu Thr Met Asp Pro Leu
                245                 250                 255

Lys Glu Ile Asp Asp Ala Ile Ala Lys Ile Asp Asp Ile Arg Gly Ser
                260                 265                 270

Leu Gly Ala Thr Gly Asn Arg Leu Gly Ser Val Ile Asn Ser Leu Ser
            275                 280                 285

Thr Thr Ile Ala Asn Leu Thr Gln Ser Arg Ser Asn Ile Leu Asp Ala
        290                 295                 300

Asp Phe Ala Thr Glu Val Ser Met Met Asn Arg Ala Asn Ile Leu Gln
305                 310                 315                 320

Gly Ala Gly Thr Ala Val Leu Ala Gly Ala Asn Ala Val Pro
                325                 330

<210> SEQ ID NO 19
<211> LENGTH: 199
<212> TYPE: PRT
<213> ORGANISM: Borrelia garinii

<400> SEQUENCE: 19

Asn Thr Ser Lys Ala Ile Asn Phe Ile Gln Thr Thr Glu Gly Asn Leu
1               5                   10                  15

Asn Glu Val Glu Lys Val Leu Val Arg Met Lys Glu Leu Ala Val Gln
                20                  25                  30

Ser Gly Asn Gly Thr Tyr Ser Asp Ala Asp Arg Gly Ser Ile Gln Ile
            35                  40                  45

Glu Ile Glu Gly Leu Thr Asp Glu Ile Asn Arg Ile Ala Asp Gln Ala
        50                  55                  60

Gln Tyr Asn Gln Met His Met Leu Ser Asn Lys Ser Ala Ser Gln Asn
65                  70                  75                  80

Val Arg Thr Ala Glu Glu Leu Gly Met Gln Pro Ala Lys Ile Asn Thr
                85                  90                  95

Pro Ala Ser Leu Ser Gly Ser Gln Ala Ser Trp Thr Leu Arg Val His
            100                 105                 110

Val Gly Ala Asn Gln Asp Glu Ala Ile Ala Val Asn Ile Tyr Ala Ala
        115                 120                 125

Asn Val Ala Asn Leu Phe Ser Gly Glu Gly Ala Gln Ala Ala Gln Thr
    130                 135                 140
```

```
Ala Pro Val Gln Glu Gly Ala Gln Gln Glu Gly Ala Gln Gln Pro Ala
145                 150                 155                 160

Pro Ala Thr Ala Pro Ser Gln Gly Gly Val Asn Ser Pro Val Asn Val
                165                 170                 175

Thr Thr Thr Val Asp Ala Asn Thr Ser Leu Ala Lys Ile Glu Asn Ala
            180                 185                 190

Ile Arg Met Ile Ser Asp Gln
        195

<210> SEQ ID NO 20
<211> LENGTH: 199
<212> TYPE: PRT
<213> ORGANISM: Borrelia garinii

<400> SEQUENCE: 20

Asn Thr Ser Lys Ala Ile Asn Phe Ile Gln Thr Thr Glu Gly Asn Leu
1               5                   10                  15

Asn Glu Val Glu Lys Val Leu Val Arg Met Lys Glu Leu Ala Val Gln
            20                  25                  30

Ser Gly Asn Gly Thr Tyr Ser Asp Ala Asp Arg Gly Ser Ile Gln Ile
        35                  40                  45

Glu Ile Glu Gly Leu Thr Asp Glu Ile Asn Arg Ile Ala Asp Gln Ala
    50                  55                  60

Gln Tyr Asn Gln Met His Met Leu Ser Asn Lys Ser Ala Ser Gln Asn
65                  70                  75                  80

Val Arg Thr Ala Glu Glu Leu Gly Met Gln Pro Ala Lys Ile Asn Thr
                85                  90                  95

Pro Ala Ser Leu Ser Gly Ser Gln Ala Ser Trp Thr Leu Arg Val His
            100                 105                 110

Val Gly Ala Asn Gln Asp Glu Ala Ile Ala Val Asn Ile Tyr Ala Ala
        115                 120                 125

Asn Val Ala Asn Leu Phe Ser Gly Glu Gly Ala Gln Ala Ala Gln Thr
    130                 135                 140

Ala Pro Val Gln Glu Gly Ala Gln Gln Glu Gly Ala Gln Gln Pro Ala
145                 150                 155                 160

Pro Ala Thr Ala Pro Ser Gln Gly Gly Val Asn Ser Pro Val Asn Val
                165                 170                 175

Thr Thr Thr Val Asp Ala Asn Thr Ser Leu Ala Lys Ile Glu Asn Ala
            180                 185                 190

Ile Arg Met Ile Ser Asp Gln
        195

<210> SEQ ID NO 21
<211> LENGTH: 164
<212> TYPE: PRT
<213> ORGANISM: Babesia bovis

<400> SEQUENCE: 21

Met Ala Asp Trp Val Pro Thr Ile Lys Gln Leu Ala Leu Ala Asp Asn
1               5                   10                  15

Ala Cys Tyr Gly Cys Gly Ile Ala Asn Ala Glu Asp Gly Glu Ile Phe
            20                  25                  30

Ser Ala Ala Asp Ile Asp His Asp Asp Leu Cys Trp Asp Ser Val Tyr
        35                  40                  45

Arg Asp Pro Tyr Glu Phe Glu Ala Thr Asp Glu Asn Gly Gln Pro Ile
    50                  55                  60
```

```
Lys His Gln Ile Thr Glu Lys Ala Thr Ile Met Glu Val Phe Glu Lys
 65                  70                  75                  80

Arg Arg Ser Ser Ile Gly Ile Phe Ile Gly Gly Asn Lys Tyr Thr Phe
                 85                  90                  95

Ala Asn Tyr Asp Asp Asp Cys Pro Val Gly Asp Tyr Thr Phe Lys Cys
            100                 105                 110

Val Ser Ala Ala Lys Asn Lys Gly Gly Ala His Leu Val Lys Thr Pro
        115                 120                 125

Gly Gly Tyr Ile Val Ile Cys Val Phe Asp Glu Asn Arg Gly Gln Asn
130                 135                 140

Lys Thr Ala Ser Arg Met Ala Ala Phe Ala Leu Ala Glu Tyr Met Ala
145                 150                 155                 160

Ala Asn Gly Tyr

<210> SEQ ID NO 22
<211> LENGTH: 130
<212> TYPE: PRT
<213> ORGANISM: Arabidopsis thaliana

<400> SEQUENCE: 22

Met Ser Trp Gly Thr Tyr Val Asp Asp His Leu Met Cys Asp Val Ala
1               5                   10                  15

Gly Asn Arg Leu Thr Ala Ala Ile Leu Gly Gly Asp Gly Ser Val
            20                  25                  30

Trp Ala Gly Ser Asn Asn Phe Pro Gln Val Lys Pro Glu Glu Ile Gln
            35                  40                  45

Gly Ile Lys Asp Asp Phe Thr Thr Pro Gly Thr Leu Ala Pro Thr Gly
 50                  55                  60

Leu Phe Leu Gly Gly Asn Lys Tyr Met Val Ile Gly Glu Pro Asn
 65                  70                  75                  80

Ala Val Ile Arg Gly Lys Lys Gly Ala Gly Gly Val Thr Ile Lys Lys
                 85                  90                  95

Thr Thr Leu Ala Leu Val Phe Gly Ile Tyr Asp Glu Pro Met Thr Pro
            100                 105                 110

Gly Gln Cys Asn Met Val Val Glu Asn Leu Gly Glu Tyr Leu Ile Glu
        115                 120                 125

Ser Gly
    130

<210> SEQ ID NO 23
<211> LENGTH: 133
<212> TYPE: PRT
<213> ORGANISM: Vaccinia virus

<400> SEQUENCE: 23

Met Ala Glu Trp His Lys Ile Ile Glu Asp Ile Ser Lys Asn Asn Lys
1               5                   10                  15

Phe Glu Asp Ala Ala Ile Val Asp Tyr Lys Thr Thr Lys Asn Val Leu
            20                  25                  30

Ala Ala Ile Pro Asn Arg Thr Phe Ala Lys Ile Asn Pro Gly Glu Ile
            35                  40                  45

Ile Pro Leu Ile Thr Asn Arg Asn Ile Leu Lys Pro Leu Ile Gly Gln
 50                  55                  60

Lys Tyr Cys Ile Val Tyr Thr Asn Ser Leu Met Asp Glu Asn Thr Tyr
 65                  70                  75                  80
```

Ala Met Glu Leu Leu Thr Gly Tyr Ala Pro Val Ser Pro Ile Val Ile
            85                  90                  95

Ala Arg Thr His Thr Ala Leu Ile Phe Leu Met Gly Lys Pro Thr Thr
            100                 105                 110

Ser Arg Arg Asp Val Tyr Arg Thr Cys Arg Asp His Ala Thr Arg Val
            115                 120                 125

Arg Ala Thr Gly Asn
            130

<210> SEQ ID NO 24
<211> LENGTH: 133
<212> TYPE: PRT
<213> ORGANISM: Taterapox virus

<400> S

Arg Ala Thr Gly Asn
    130

<210> SEQ ID NO 26
<211> LENGTH: 131
<212> TYPE: PRT
<213> ORGANISM: Cinnamomum camphora

<400> SEQUENCE: 26

Met Ser Trp Gln Ala Tyr Val Asp Asp His Leu Met Cys Asp Ile Asp
1               5                   10                  15

Gly Gly His Leu Thr Ala Ala Ile Val Gly His Asp Gly Ser Val
            20                  25                  30

Trp Ala Gln Ser Asp Ser Phe Pro Gly Phe Lys Pro Glu Glu Ile Asn
            35                  40                  45

Gly Ile Met Asn Asp Phe Ala Glu Pro Gly Tyr Leu Ala Pro Thr Gly
    50                  55                  60

Leu Tyr Leu Gly Gly Thr Lys Tyr Met Val Ile Gln Gly Glu Pro Gly
65                  70                  75                  80

Ala Val Ile Arg Gly Lys Lys Gly Ser Gly Gly Ile Thr Ile Lys Lys
                85                  90                  95

Thr Gly Gly Ala Leu Ile Phe Gly Ile Tyr Asp Glu Pro Leu Thr Pro
            100                 105                 110

Gly Gly Cys Asn Met Ile Val Glu Arg Leu Gly Asp Tyr Leu Ile Glu
        115                 120                 125

Gly Gly Met
    130

<210> SEQ ID NO 27
<211> LENGTH: 130
<212> TYPE: PRT
<213> ORGANISM: Solanum tuberosum

<400> SEQUENCE: 27

Met Ser Trp Gln Thr Tyr Val Asp Glu His Leu Leu Cys Glu Ile Glu
1               5                   10                  15

Gly Asn His Leu Thr Ser Ala Ala Ile Val Gly Gln Asp Gly Thr Val
            20                  25                  30

Trp Ala Gly Ser Ala Asn Phe Pro Gln Phe Lys Pro Glu Glu Ile Ser
            35                  40                  45

Gly Ile Met Asn Asp Phe Ala Glu Pro Gly Thr Leu Ala Pro Thr Gly
    50                  55                  60

Leu Tyr Leu Gly Gly Thr Lys Tyr Met Val Ile Gln Gly Glu Pro Gly
65                  70                  75                  80

Ala Val Ile Arg Gly Lys Lys Gly Pro Gly Gly Ile Thr Ile Lys Lys
                85                  90                  95

Thr Asn Gln Ala Leu Ile Ile Gly Ile Tyr Asp Glu Pro Met Thr Pro
            100                 105                 110

Gly Gln Cys Asn Met Ile Val Glu Arg Leu Gly Asp Tyr Leu Val Glu
        115                 120                 125

Gln Gly
    130

<210> SEQ ID NO 28
<211> LENGTH: 133
<212> TYPE: PRT
<213> ORGANISM: Monkeypox virus

```
<400> SEQUENCE: 28

Met Ala Glu Trp His Lys Ile Ile Glu Asp Ile Ser Lys Asn Asn Lys
1               5                   10                  15

Phe Glu Asp Ala Ala Ile Val Asp Tyr Lys Thr Thr Lys Asn Val Leu
            20                  25                  30

Ala Ala Ile Pro Asn Arg Thr Phe Ala Lys Ile Asn Pro Gly Glu Val
        35                  40                  45

Ile Pro Leu Ile Thr Asn His Asn Ile Leu Lys Pro Leu Ile Gly Gln
    50                  55                  60

Lys Phe Cys Ile Val Tyr Thr Asn Ser Leu Met Asp Glu Asn Thr Tyr
65                  70                  75                  80

Ala Met Glu Leu Leu Thr Gly Tyr Ala Pro Val Ser Pro Ile Val Ile
                85                  90                  95

Ala Arg Thr His Thr Ala Leu Ile Phe Leu Met Gly Lys Pro Thr Thr
            100                 105                 110

Ser Arg Arg Asp Val Tyr Arg Thr Cys Arg Asp His Ala Thr Arg Val
        115                 120                 125

Arg Ala Thr Gly Asn
        130

<210> SEQ ID NO 29
<211> LENGTH: 9
<212> TYPE: PRT
<213> ORGANISM: Artificial Sequence
<220> FEATURE:
<223> OTHER INFORMATION: Synthetic

<400> SEQUENCE: 29

Leu Pro Tyr Leu Gly Trp Leu Val Phe
1               5

<210> SEQ ID NO 30
<211> LENGTH: 45
<212> TYPE: PRT
<213> ORGANISM: Artificial Sequence
<220> FEATURE:
<223> OTHER INFORMATION: Synthetic

<400> SEQUENCE: 30

Met Leu Pro Tyr Leu Gly Trp Leu Val Phe Ala Gln His Pro Asn Ala
1               5                   10                  15

Glu Leu Leu Lys His Tyr Leu Phe Arg Asn Leu Ser Pro Ser Tyr Val
            20                  25                  30

Tyr His Gln Phe Ile Pro Asn Pro Leu Leu Gly Leu Asp
        35                  40                  45

<210> SEQ ID NO 31
<211> LENGTH: 17
<212> TYPE: PRT
<213> ORGANISM: Salmonella typhimurium

<400> SEQUENCE: 31

Val Leu Ala Gln Ala Asn Gln Val Pro Gln Asn Val Leu Ser Leu Leu
1               5                   10                  15

Arg

<210> SEQ ID NO 32
<211> LENGTH: 19
<212> TYPE: PRT
<213> ORGANISM: Salmonella typhimurium
```

```
<400> SEQUENCE: 32

Thr Ser Val Leu Ala Gln Ala Asn Gln Val Pro Gln Asn Val Leu Ser
1               5                   10                  15

Leu Leu Arg
```

METHODS AND COMPOSITIONS FOR CANCER IMMUNOTHERAPY USING FLAGELLIN-TUMOR ASSOCIATED ANTIGEN FUSION PROTEIN EXPRESSING TUMOR CELLS

FIELD OF THE INVENTION

The present invention is related to methods for inducing an anti-tumor immune response by immunizing a mammal with a composition comprising a tumor cell which expresses a Nod-like receptor (NLR) and/or a Toll-like receptor (TLR) ligand-tumor associated antigen (TAA) fusion protein or with an activated DC which has internalized a tumor cell which expresses an NLR- and/or TLR ligand-TAA fusion protein.

BACKGROUND OF INVENTION

Multicellular organisms have developed two general systems of immunity to infectious agents. The two systems are innate or natural immunity (usually referred to as "innate immunity") and adaptive (acquired) or specific immunity. The major difference between the two systems is the mechanism by which they recognize infectious agents. Recent studies have demonstrated that the innate immune system plays a crucial role in the control of initiation of the adaptive immune response and in the induction of appropriate cell effector responses (Fearon et al. Science 1996; 272:50-53 and Medzhitov et al. Cell 1997; 91:295-298).

The innate immune system uses a set of germline-encoded receptors for the recognition of conserved molecular patterns present in microorganisms. These molecular patterns occur in certain constituents of microorganisms including: lipopolysaccharides, peptidoglycans, lipoteichoic acids, phosphatidyl cholines, bacterial proteins (e.g., flagellin), including lipoproteins, bacterial DNAs, viral single and double-stranded RNAs, unmethylated CpG-DNAs, mannans, and a variety of other bacterial and fungal cell wall components. Such molecular patterns can also occur in other molecules such as plant alkaloids. These targets of innate immune recognition are called Pathogen Associated Molecular Patterns (PAMPs) since they are produced by microorganisms and not by the infected host organism (Janeway et al. Cold Spring Harb. Symp. Quant. Biol. 1989; 54:1-13 and Medzhitov et al. Curr. Opin Immunol. 1997; 94:4-9). PAMPs are discrete molecular structures that are shared by a large group of microorganisms. They are conserved products of microbial metabolism, which are not subject to antigenic variability (Medzhitov et al. Cur Op Immun 1997; 9:4).

The receptors of the innate immune system that recognize PAMPs are called Pattern Recognition Receptors (PRRs) (Janeway et al. Cold Spring Harb. Symp. Quant. Biol. 1989; 54:1-13 and Medzhitov et al. Curr. Opin. Immunol. 1997; 94:4-9). These receptors vary in structure and belong to several different protein families. Some of these receptors recognize PAMPs directly (e.g., TLR3, collectins), while others (e.g., complement receptors) recognize the products generated by PAMP recognition.

Cellular PRRs are expressed on effector cells of the innate immune system, including cells that function as professional antigen-presenting cells (APC) in adaptive immunity. Such effector cells include, but are not limited to, macrophages, dendritic cells, B lymphocytes, and surface epithelia. This expression profile allows PRRs to directly induce innate effector mechanisms, and also to alert the host organism to the presence of infectious agents by inducing the expression of a set of endogenous signals, such as inflammatory cytokines and chemokines. This latter function allows efficient mobilization of effector forces to combat the invaders. Examples of PRRs include Nod-like receptors (NLRs) and Toll-like receptors (TLRs).

NLRs are cytoplasmic proteins that may have a variety of functions in regulation of inflammatory and apoptotic responses. NLRs are composed of conserved "modules" including a central nucleotide-binding oligomerization domain and a series of tandem leucine-rich repeats. NLRs are encoded by genes from a large gene family present in many different animal species; there are more than 20 NLR genes in humans. Many are thought to serve as PRRs which sense microbial products in the cytoplasm of cells, although some members have different functions. The ligands are currently known for the NLRs, NLRC1 (NOD1) and NLRC2 (NOD2). NLRC1 recognizes a molecule called Meso-diaminopimelic acid (meso-DAP), which is a peptidoglycan constituent of only Gram negative bacteria. NLRC2 proteins recognize intracellular MDP (muramyl dipeptide), which is a peptidoglycan constituent of both Gram positive and Gram negative bacteria. These proteins transduce signals in the pathway of NF-κB and MAP kinases. To do this, they interact with the serine-threonine kinase called RIPK2 via an N-terminal CARD domains and interact with microbial molecules by means of a C-terminal leucine-rich repeat (LRR) region [Strober et al., Signalling pathways and molecular interactions of NOD 1 and NOD2. Nat Rev Immunol. 2006, Volume 6(1):9-20.] NLRC4 (IPAF) has also been shown to activate caspase-1 in response to bacteria. Further, anthrax toxin activates NLRP1 (previously called NALP1), and *Staphylococcus aureus* toxins such as alpha-hemolysin (GenBank Accession No. AAA26598) (SEQ ID NO: 1) activate NLRP3. Other NLRs such as NAIP have also been shown to activate caspase-1 in response to *Salmonella* and *Legionella*. [SEE, Inohara et al., NOD-LRR proteins: role in host-microbial interactions and inflammatory disease. Annu Rev Biochem. 2005, Volume 74:355-83; Strober et al., Signalling pathways and molecular interactions of NOD1 and NOD2. Nat Rev Immunol. 2006, Volume 6(1):9-20; Chen G, Shaw M H, Kim Y G, Nuñez G. Annu Rev Pathol. 2009, 4:365-98; Martinon F, Mayor A, Tschopp J. Annu Rev Immunol. 2009; 27:229-65].

The best characterized class of cellular PRRs are members of the family of Toll-like receptors (TLRs), so called because they are homologous to the *Drosophila* Toll protein which is involved both in dorsoventral patterning in *Drosophila* embryos and in the immune response in adult flies (Lemaitre et al. Cell 1996; 86:973-83). At least 12 mammalian TLRs, TLRs 1 through 11 and TLR13, have been identified to date (see, for example, Medzhitov et al. Nature 1997; 388:394-397; Rock et al. Proc Natl Acad Sci USA 1998; 95:588-593; Takeuchi et al. Gene 1999; 231:59-65; and Chuang and Ulevitch. Biochim Biophys Acta. 2001; 1518:157-61). Activation of signal transduction pathways by TLRs leads to the induction of various genes including inflammatory cytokines, chemokines, major histocompatability complex, and co-stimulatory molecules (e.g., B7). For example, activation of TLR4 can induce the secretion of tumor necrosis factor (TNF) and of the interleukins IL-1 and IL-6 as part of an antibacterial response, and can induce the secretion of the interferons INFα and INFβ as part of an anti viral response.

TLR signaling consists of at least two distinct pathways: a MyD88-dependent pathway that leads to the production of inflammatory cytokines, and a MyD88-independent pathway associated with the stimulation of IFN-β and the maturation of dendritic cells. The MyD88-dependent pathway is common to all TLRs, except TLR3 [Adachi O. et al., 1998. Targeted disruption of the MyD88 gene results in loss of IL-1- and IL-18-mediated function. Immunity. 9(1):143-50.]. Upon activation by microbial antigens, TLRs induce the recruitment of MyD88 via its TIR domain which in turn recruits IRAK1 and IRAK4 and leads to complex downstream signaling cascades leading to the phosphorylation of IκB and the subsequent nuclear localization of NF-κB. Activation of NF-κB triggers the production of pro-inflammatory cytokines such as TNF-α, IL-1 and IL-12.

In mammalian organisms, TLRs have been shown to recognize PAMPs such as the bacterial products LPS (Schwandner et al. J. Biol. Chem. 1999; 274:17406-9 and Hoshino et al. J. Immunol. 1999; 162:3749-3752), lipoteichoic acid (Schwandner et al. J. Biol. Chem. 1999; 274:17406-9), peptidoglycan (Yoshimura et al. J. Immunol. 1999; 163:1-5), lipoprotein (Aliprantis et al. Science 1999; 285:736-9), CpG-DNA (Hemmi et al. Nature 2000; 408:740-745), and flagellin (Hayashi et al. Nature 2001; 410:1099-1103), as well as the viral product double stranded RNA (Alexopoulou et al. Nature 2001; 413:732-738) and the yeast product zymosan (Underhill. J Endotoxin Res. 2003; 9:176-80). For example, TLR2 is essential for the recognition of a variety of PAMPs, including bacterial lipoproteins, peptidoglycan, and lipoteichoic acids. TLR3 is implicated in virus-derived double-stranded RNA. TLR4 is predominantly activated by lipopolysaccharide. TLR9 is required for response to unmethylated CpG DNA. Recently, TLR7 and TLR8 have been shown to recognize single stranded RNA molecules (Hornung V. et al. Handb Exp Pharmacol. 2008; (183):71-86), and small synthetic antiviral molecules (Jurk M. et al. Nat Immunol 2002; 3:499). TLR11 detects profilin-like protein (PLP). Furthermore, TLR5 detects bacterial flagellin.

Flagellin is a protein expressed by a variety of flagellated bacteria (*Salmonella typhimurium* for example) as well as non-flagellated bacteria (such as *Escherichia coli*). Sensing of flagellin by cells of the innate immune system (dendritic cells, macrophages, etc) is mediated by the Toll-like receptor 5 (TLR5) as well as by Nod-like receptors (NLRs) Ipaf and Naip5 (Franchi et al (2006) Nat Immunol 7(6):576-582; Miao et al (2006) Nat Immunol 7(6):569-575; and Ren et al (2006) PLoS Pathog 2(3):e18). Various reports have described the role of TLRs and NLRs in the activation of innate immune response and adaptive immune response. Thus, it has been suggested that flagellin, like other TLR ligands, could be a relevant adjuvant in immunotherapies.

*Bacillus anthracis* is the bacterium that causes anthrax. The bacterium secretes a toxin called anthrax lethal toxin, which is the major cause of pathogenesis, and is composed of a protective antigen and a lethal factor (Stephen, J. Anthrax toxin. 1981. Pharmacol. Ther. 12, 501-513). It was recently shown that lethal factor component of anthrax toxin enters the cytosol of macrophages and other cell types, and is recognized by the NLR protein Nalp1 or NLRP1 and mediates cell death (Boyden et al. 2006 Nat Genet. 38:240-244).

*Staphylococcus aureus* is a Gram positive bacterium responsible for a wide variety of superficial as well as serious life-threatening infections (Lowy et al. 1998. *N. Engl. J. Med.* 339: 520-525). *S. aureus* secretes many toxins among which α-hemolysin has been implicated in the pathogenesis of *S. aureus* necrotizing pneumonia and various other symptoms in animal models. α-Hemolysin is secreted as a 33-kDa monomer and oligomerizes, forming heptameric transmembrane pores (Song et al. 1996 Science 274: 1859-1866). It was recently shown that α-hemolysin is recognized by the NLR-protein NLRP3, and initiates cell death (Craven et al. 2009 PLoS One 4:e7446; Munoz-Planillo et al. 2009 183:3942-3948).

TLR ligands have been exploited as adjuvant in numerous therapy regimens [Koski, G. K. et al., Reengineering dendritic cell-based anti-cancer vaccines. Immunol Rev 222, 256 (2008)]. For example, local administration of live bacilli Calmette-Guerin (BCG), which stimulate TLR2 and TLR4, has been proven to be beneficial in the treatment of tumors such as bladder cancer [Herr, H. W. et al., Intravesical *bacillus* Calmette-Guerin therapy prevents tumor progression and death from superficial bladder cancer: ten-year follow-up of a prospective randomized trial. J Clin Oncol 13 (6), 1404 (1995)]. Imiquimod, an agonist for TLR7, is approved for the treatment of basal cell carcinoma and precursor lesion of cutaneous squamous cell carcinoma [Herr, H. W. et al., Intravesical *bacillus* Calmette-Guerin therapy prevents tumor progression and death from superficial bladder cancer: ten-year follow-up of a prospective randomized trial. J Clin Oncol 13 (6), 1404 (1995)]. Similarly, the TLR9 ligand CpG has also been used in different mono-therapies, combination therapies and Phase I/II trials [Dougan, M. and Dranoff, G., Immune Therapy for Cancer. Annu Rev Immunol (2008)].

In peptides-based vaccines, the use of TLR ligands in conjunction with long peptides containing helper and cytotoxic T lymphocytes (CTL) epitopes, has shown to be efficient at promoting helper CD4+ T cells [Melief, C. J. et al., Effective therapeutic anticancer vaccines based on precision guiding of cytolytic T lymphocytes. Immunol Rev 188, 177 (2002); Jackson, D. C. et al., A totally synthetic vaccine of generic structure that targets Toll-like receptor 2 on dendritic cells and promotes antibody or cytotoxic T cell responses. Proc Natl Acad Sci USA 101 (43), 15440 (2004)]. Similarly to TLR ligands, many adjuvants used in human vaccine also include ligands for NLRs and can activate DCs [Martinon, F., Mayor, A., and Tschopp, J., The inflammasomes: guardians of the body. Annu Rev Immunol 27, 229 (2009)]. Further, recently it has been discovered that TLR ligands enhance presentation of phagocytosed antigens within major histocompatibility class II MHC molecules [Blander, J. M. and Medzhitov, R., Nature (2006), Vol. 440, pp. 808].

Recent evidence demonstrates that fusing a polypeptide ligand specific for a Toll-like receptor (TLR) to an antigen of interest generates a vaccine that is more potent and selective than the antigen alone. It has been previously shown that immunization with recombinant TLR-ligand:antigen fusion proteins: a) induces antigen-specific T-cell and B-cell responses comparable to those induced by the use of conventional adjuvant, b) results in significantly reduced non-specific inflammation; and c) results in CD8+ T-cell-mediated protection that is specific for the fused antigen epitopes (See, for example US published patent applications 2002/0061312 and 2003/0232055 to Medzhitov, and US published patent application 2003/0175287 to Medzhitov and Kopp). For example, mice immunized with a fusion protein consisting of the polypeptide PAMP BLP linked to *Leishmania major* antigens mounted a Type 1 immune response characterized by antigen-induced production of γ-interferon and antigen-specific IgG2a (Cote-Sierra et al. Infect Immun 2002; 70:240-248). The response was protective, as demonstrated in experiments in which immunized mice developed smaller lesions than control mice did following challenge with live *L. major*. Furthermore, flagellin fusion to well defined antigens promotes protective immunity in mice [Huleatt, J. W. et al., in Vaccine (2007), Vol. 25, pp. 763; Huleatt, J. W. et al., in Vaccine (2008), Vol. 26, pp. 201.] and activates human DCs [Arimilli, S. et al., Engineered Expression of the TLR5Ligand Flagellin Enhances Paramyxovirus Activation of Human Dendritic Cell Function. J Virol (2008)].

While the above fusion proteins provided a lot of promise based on their in vitro data, thus far it has proven difficult to achieve long-lasting, effective immunity, including generation of both CD4+ and CD8+ T cell responses, to the desired antigen in clinical trials using such fusion proteins. CD8+ T cells (such as cytotoxic T lymphocytes (CTLs)) directly kill tumor cells and are important for tumor rejection. CD4 T helper (Th) cell responses can also contribute to anti-tumor activity through direct killing of tumors, by supporting both the activation and long-term maintenance of CD8+ T cells, and through the production of cytokines. Th cells can also support the humoral immune response mediated by B cells [Koski et al. (2008) supra].

Immunotherapy, if successful, would be particularly appealing for use as a cancer treatment, for which new and better treatments are desperately needed. The last decade has witnessed steady reductions in the death rates for many types of cancer. These reductions are largely due to improvements in early detection, advanced surgical techniques, refinements in the administration of radiation therapies, and the discovery of new, molecular-targeted chemotherapeutic agents. However, countless instances occur either where tumors are not amenable to any existing therapy or they respond initially only to recur in forms resistant to front-line therapies, leaving limited treatment options. Moreover, immunotherapies would be suitable to prevent relapse.

The development of novel treatment modalities will greatly benefit cancer patients. One such modality is immunotherapy, which posits that the immune system can be enlisted in the fight against cancer. There has existed for some time compelling evidence that cellular and molecular agents of the immune system are capable of attacking tumors, and experimental immunotherapeutic interventions have sought to take advantage of each of them. Although most immunotherapy trials have yielded somewhat disappointing results, there are some examples of success, such as recent T-cell adoptive therapy trials. These treatments have proven that immunotherapy can induce pronounced tumor regressions that are associated with prolonged survival for advanced melanoma [Koski et al. (2008) Immunological Reviews 222: 256-276]. At least for relatively advanced melanoma, such outcomes are currently superior to any other therapeutic modality available. However, this type of therapy involves the cultivation of huge numbers of patient lymphocytes, which requires uncommon technical expertise and specialized facilities. Therefore, less labor intensive forms of immunotherapy, such as vaccine modalities, are desirable for more widespread implementation.

Unfortunately, vaccine strategies have underperformed these more labor-intensive adoptive immunotherapy approaches. Breakthroughs in the understanding of tumor immunology are needed to advance vaccine-based immunotherapy to this next level. One substantial hope for the development of cancer vaccines came with the development of methods to culture human and mouse dendritic cells (DCs) [Koski et al. (2008) supra]. Because DCs were considered the most efficient known cells for the presentation of antigen to T cells, it was therefore supposed (based on some early work with murine models) that it might be relatively easy to pulse tumor antigens onto DCs and use these cells to successfully vaccinate against tumors [Zitvogel L, et al. Therapy of murine tumors with tumor peptide-pulsed dendritic cells: dependence on T cells, B7 costimulatiori, and T helper cell 1-associated cytokines. J Exp Med 1996; 183:87-97.]. The primary source for human DC precursors was the blood and bone marrow, but the first methods produced only immature DCs. Later, ways were found to mature these cells, which usually involved a second step culture with additional cytokines [Zhou L F, Tedder T F. CD141 blood monocytes can differentiate into functionally mature CD831 dendritic cells. Proc Natl Acad Sci USA 1996; 93:2588-2592.]. Both immature and mature cells have been tested in clinical trials to treat various malignancies. Whereas occasional clinically relevant responses were observed, the overall results have been disappointing [Koski et al. (2008) supra].

There is therefore a need to develop improved compositions and methods for cancer immunotherapy. The present invention provides such methods.

SUMMARY OF INVENTION

In certain aspects, the present invention provides a composition comprising a dendritic cell (DC), wherein said DC has internalized a tumor cell expressing a fusion protein, said fusion protein comprising a Toll-like receptor (TLR) ligand and a tumor-associated antigen (TAA).

In other aspects, the present invention provides a composition comprising a dendritic cell (DC), wherein said DC has internalized a tumor cell expressing a fusion protein, said fusion protein comprising a Nod-like receptor (NLR) ligand and a tumor-associated antigen (TAA).

In yet another aspect, the present invention provides a composition comprising a dendritic cell (DC), wherein said DC has internalized a tumor cell expressing a fusion protein, said fusion protein comprising a Nod-like receptor (NLR) ligand, a Toll-like receptor (TLR) ligand and a tumor-associated antigen (TAA).

In one embodiment, the present invention provides a method for inducing an anti-tumor immune response in a mammal comprising administering to said mammal in need thereof an immunogenically effective amount of a composition comprising a dendritic cell (DC), wherein said DC has internalized a tumor cell expressing a fusion protein, said fusion protein comprising a Toll-like receptor (TLR) ligand and a tumor-associated antigen (TAA). In another embodiment, the present invention provides a method for inducing an anti-tumor immune response in a mammal comprising administering to said mammal in need thereof an immunogenically effective amount of a composition comprising a dendritic cell (DC), wherein said DC has internalized a tumor cell expressing a fusion protein, said fusion protein comprising a Nod-like receptor (NLR) ligand and a tumor-associated antigen (TAA). In another embodiment, the present invention provides a method for inducing an anti-tumor immune response in a mammal comprising administering to said mammal in need thereof an immunogenically effective amount of a composition comprising a dendritic cell (DC), wherein said DC has internalized a tumor cell expressing a fusion protein, said fusion protein comprising a Nod-like receptor (NLR) ligand, a Toll-like receptor (TLR) ligand and a tumor-associated antigen (TAA).

In a specific embodiment, the present invention provides a method for treating a cancer in a patient comprising administering to said patient in need of such treatment a composition comprising a dendritic cell (DC), wherein said DC has internalized a tumor cell expressing a fusion protein, said fusion protein comprising a Toll-like receptor (TLR) ligand and a tumor-associated antigen (TAA), wherein said composition is administered in an effective amount for eliciting an anti-tumor immune response. In another specific embodiment, the present invention provides a method for treating a cancer in a patient comprising administering to said patient in need of such treatment a composition comprising a dendritic cell (DC), wherein said DC has internalized a tumor cell expressing a fusion protein, said fusion protein comprising a Nod-like receptor (NLR) ligand and a tumor-associated antigen (TAA), wherein said composition is administered in an effective amount for eliciting an anti-tumor immune response.

In another embodiment, the present invention provides a method for inducing an anti-tumor immune response in a mammal comprising administering to said mammal in need thereof an immunogenically effective amount of a composition comprising a dendritic cell (DC), wherein said DC has internalized a tumor cell expressing a fusion protein, said fusion protein comprising a Nod-like receptor (NLR) ligand, a Toll-like receptor (TLR) ligand and a tumor-associated antigen (TAA).

In a specific embodiment, the present invention provides a method for treating a cancer in a patient comprising administering to said patient in need of such treatment a composition comprising a dendritic cell (DC), wherein said DC has internalized a tumor cell expressing a fusion protein, said fusion protein comprising a Nod-like receptor (NLR) ligand, a Toll-like receptor (TLR) ligand and a tumor-associated antigen (TAA), wherein said composition is administered in an effective amount for eliciting an anti-tumor immune response.

In one aspect, the invention provides a method for inducing an anti-tumor immune response in a mammal comprising administering to said mammal in need thereof an immunogenically effective amount of a composition comprising a tumor cell expressing a fusion protein, wherein said fusion protein comprises a TLR ligand and a tumor-associated antigen (TAA).

In another aspect, the invention provides a method for treating a cancer in a patient comprising administering to said patient in need of such treatment a composition comprising a tumor cell expressing a fusion protein, wherein said fusion protein comprises a Toll-like receptor (TLR) ligand and a tumor-associated antigen (TAA), in an effective amount for eliciting an anti-tumor immune response.

In one embodiment, the invention provides a method for inducing an anti-tumor immune response in a mammal comprising administering to said mammal in need thereof an immunogenically effective amount of a composition comprising a tumor cell expressing a fusion protein, wherein said fusion protein comprises a Nod-like receptor (NLR) ligand and a tumor-associated antigen (TAA).

In yet another embodiment, the invention provides a method for treating a cancer in a patient comprising administering to said patient in need of such treatment a composition comprising a tumor cell expressing a fusion protein in an effective amount for eliciting an anti-tumor immune response, wherein said fusion protein comprises a Nod-like receptor (NLR) ligand and a tumor-associated antigen (TAA).

In one aspect, the invention provides a method for inducing an anti-tumor immune response in a mammal comprising administering to said mammal in need thereof an immunogenically effective amount of a composition comprising a tumor cell expressing a fusion protein, wherein said fusion protein comprises a fusion protein, wherein said fusion protein comprises a said fusion protein comprising a Nod-like receptor (NLR) ligand, a Toll-like receptor (TLR) ligand and a tumor-associated antigen (TAA).

In another aspect, the invention provides a method for treating a cancer in a patient comprising administering to said patient in need of such treatment a composition comprising a tumor cell expressing a fusion protein, wherein said fusion protein comprises a said fusion protein comprising a Nod-like receptor (NLR) ligand, a Toll-like receptor (TLR) ligand and a tumor-associated antigen (TAA), in an effective amount for eliciting an anti-tumor immune response.

In certain of the above embodiments, the TLR ligand is a polypeptide. In certain of the above embodiments, the TLR ligand is a flagellin or profilin-like protein (PLP), or a fragment thereof.

In certain of the above embodiments, the tumor cell has been transfected with a vector expressing said fusion protein. In other embodiments, the DC is an autologous cell. In some of the above embodiments, the tumor cell is an autologous cell.

In certain of the above aspects, the tumor cell is lethally irradiated prior to internalization by said DC. In still other aspects, the DC has phagocytosed said tumor cell.

In certain of the above embodiments, the anti-tumor immune response comprises a CD4 or CD8 T cell-mediated immune response. In any of the above embodiments, the mammal or patient is a human.

In certain of the above aspects, the NLR ligand is selected from the group consisting of a flagellin, an anthrax toxin, and a *Staphylococcus aureus* toxin, or a fragment thereof.

In certain of the above embodiments, the TLR ligand is also an NLR ligand. In other embodiments, the NLR ligand is also a TLR ligand. In some aspects of the invention, the fusion protein comprising a TAA and a TLR ligand further comprises a distinct NLR ligand. In other aspects of the invention, the fusion protein comprising a TAA and an NLR ligand further comprises a distinct TLR ligand.

In some embodiments, the TLR ligand is profilin-like protein (PLP) and said NLR ligand is anthrax toxin or a fragment thereof. In certain of the above aspects, the tumor cell is lethally irradiated.

In some embodiments, the TLR ligand is profilin-like protein (PLP) and said NLR ligand is the *Staphylococcus aureus* α-hemolysin, or a fragment thereof.

BRIEF DESCRIPTION OF THE DRAWINGS

FIG. 5B is a graph quantifying IL-12 secretion (ng/ml) by wild-type (wt) and MyD88$^{-/-}$ splenic dendritic cells in response to apoptotic tumor cells expressing EL4-STFOVA or EL4-OVA and in resting dendritic cells.

DETAILED DESCRIPTION OF THE INVENTION

Figure 1A:
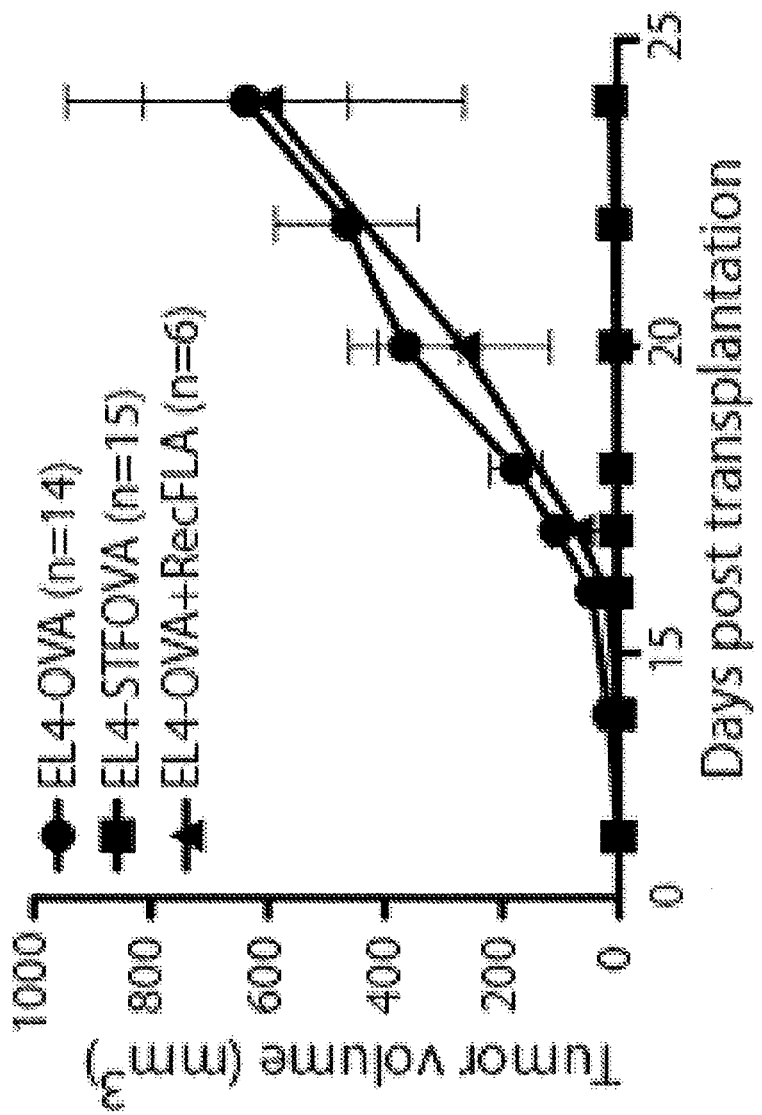
FIG. 1A is a graph showing a time course (days post injection) of tumor volume ($mm^3$) in wild type (wt) mice injected with $1 \times 10^5$ EL4 thymoma cells engineered to express either an ovalbumin (OVA) construct or an OVA-*S. typhimurium* flagellin fusion protein (STFOVA) using retroviral transduction with pMIG-IRES-GFP. In one group, EL4-OVA thymoma cells were injected mice were injected in conjunction with recombinant flagellin (RecFLA) where tumor cells and flagellin were administered together but as separate entities.

In certain embodiments, the present invention is related to immunogenic compositions comprising a tumor cell which expresses a TLR ligand-tumor associated antigen (TAA) fusion protein. In other embodiments, the present invention is related to immunogenic compositions comprising a tumor cell which expresses a Nod-like receptor (NLR) ligand-TAA fusion protein. In a preferred embodiment, a fusion protein of the invention comprises a TAA and ligand which is both a TLR ligand and an NLR ligand. In another embodiment, the fusion protein comprises at least two ligands, wherein at least one is a TLR ligand and at least one is an NLR ligand.

In certain aspects, the invention also provides methods for inducing an anti-tumor immune response by immunizing a mammal with a composition comprising a tumor cell which expresses a TLR ligand-TAA fusion protein and/or an NLR ligand-TAA fusion protein. In some aspects, the tumor cell can also express a fusion protein comprising a TAA, a TLR ligand and an NLR ligand. In other aspects, methods are provided for inducing an anti-tumor immune response by immunizing a mammal with a composition comprising a dendritic cell (DC) that has internalized (e.g., phagocytosed) a tumor cell expressing a TLR ligand-TAA fusion protein and/or a tumor cell expressing an NLR-TAA fusion protein.

In a specific embodiment, the TLR ligand of a fusion protein of the invention is a flagellin or a profilin-like protein (PLP), or fragment thereof. In other embodiments, an NLR ligand of the invention is an anthrax toxin, which activates NLRP1, or an *Staphylococcus aureus* toxin such as alpha-hemolysin, which can activate NLRP3, or a C-terminal fragment of Flagellin which is involved in Ipaf and Naip5 activation. The present invention contemplates the use of any polypeptide with the capacity to stimulate an NLR. In certain embodiments, the full length flagellin protein is both a TLR ligand and an NLR ligand.

The present invention is based in part on the discovery that compositions comprising autologous tumor cells modified ex vivo to express an NLR-ligand and/or TLR ligand-TAA fusion protein produce a much improved immune response in vivo as compared to autologous tumor cells expressing TAA co-administered (but not physically linked) with a TLR or NLR ligand. Specifically, the present Examples demonstrate that wild-type mice transplanted with tumor cells expressing flagellin (which is both a TLR ligand and an NLR ligand)-ovalbumin ((OVA)(which is a model TAA)) fusion protein fail to develop tumors, whereas mice transplanted with tumor cells expressing OVA alone or mice transplanted with tumor cells expressing OVA alone and treated with recombinant flagellin (RecFLA) develop tumors.

The compositions of the present invention are particularly effective for eliciting innate immune cell activation (e.g. macrophages, dendritic cells).

The compositions of the present invention are particularly effective for eliciting both $CD4^+$ and $CD8^+$ T cell driven immune responses.

Definitions

A "tumor cell", also known as a "neoplastic cell", refers to a cell which proliferates at an abnormally high rate. A new growth comprising tumor cells is a tumor, also known as a neoplasm. A tumor is an abnormal tissue growth, generally forming a distinct mass, that grows by cellular proliferation more rapidly than normal tissue growth. A tumor may show partial or total lack of structural organization and functional coordination with normal tissue. As used herein, a tumor is intended to encompass hematopoietic tumors as well as solid tumors. A tumor may be benign (benign tumor) or malignant (malignant tumor or cancer). A tumor or tumor tissue may also comprise non-tumor cells, e.g., vascular cells which form blood vessels to supply the tumor or tumor tissue or stroma cells. As used herein, the term "anti-tumor immune response" means an immune response, which can be innate, humoral (e.g., antibody-mediated) or cellular (e.g. CD4 or CD8 T cell mediated), or any combination thereof, directed against a tumor, tumor cell, a cancer cell, and/or antigens expressed by a tumor/cancer cell.

An "antigen" is a substance that can be recognized by an antibody, B cell or T cell. As used herein, the term "tumor associated antigen (TAA)" refers to a protein or polypeptide antigen that is expressed by a tumor cell. For example, a TAA may be one or more surface proteins or polypeptides, nuclear proteins or glycoproteins, or fragments thereof, of a tumor cell.

The definitions of protein, peptide and polypeptide are well-known in the art. The term "protein", as used herein, is synonymous with the term "peptide" or "polypeptide", and is understood to mean a chain of amino acids arranged linearly and joined together by peptide bonds between the carboxyl and amino groups of adjacent amino acid residues. Thus, the term polypeptide can refer to a full length amino acid sequence of a protein, or to a fragment thereof.

As used herein, the term "immunogenic" means that an agent is capable of eliciting a humoral or cellular immune response, and preferably both. An immunogenic composition is a composition that elicits a humoral or cellular immune response, or both, directed against one or more components of the composition, when administered to an animal having an immune system.

As used herein, the term "autologous cell" is synonymous with "syngeneic cell" and means a self cell or cell that is identical or substantially identical to an individual's self cell.

As used herein, the term "non-autologous cell" is synonymous with an "allogeneic cell" and means a non-self (non-identical) cell or xenogeneic cell.

As used herein, the term "a fusion protein of the invention" includes any of the fusion proteins described herein, such as TLR ligand-TAA fusion protein or an NLR ligand-TAA fusion protein or a fusion protein expressing a TAA, a TLR ligand and an NLR ligand. Examples of a TLR5 ligand-TAA fusion protein is a flagellin-MUC1 fusion protein or a PLP-MUC1 fusion protein. Non-limiting examples of NLR ligand-TAA fusion proteins include Flagellin-MUC1 fusion protein or anthrax toxin-MUC1 fusion protein, where MUC-1 is a TAA. Preferably, only the relevant NLR binding residues of anthrax toxin are included in the fusion protein, in order to avoid toxic effects of the full length anthrax toxin. Another example is a fusion protein comprising a TAA and a 20 amino acid C-terminal fragment of flagellin (an NLR ligand).

As used herein, the term "distinct TLR ligand" in the context of a fusion protein comprising a TLR ligand and an NLR ligand, means that the TLR ligand is a different ligand than the NLR ligand in the fusion protein. Similarly, as used herein, the term "distinct NLR ligand" in the context of a fusion protein comprising a TLR ligand and an NLR ligand, means that the NLR ligand is a different ligand than the TLR ligand in the fusion protein.

As used herein, the term "a composition of the invention" includes any of the compositions described herein, such as a composition comprising a tumor cell expressing a fusion protein of the invention or a composition comprising a dendritic cell loaded with a fusion protein of the invention.

The term "subject" or "individual" as used herein refers to an animal having an immune system, preferably a mammal (e.g., rodent, such as mouse). In particular, the term encompasses humans.

As used herein, the term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log(i.e., an order of magnitude) preferably within a factor of two of a given value.

The term "substantially identical", at the amino acid sequence level, means that the sequence identity of two amino acid sequences is at least 30%, 40%, 50%, 60%, 70%, 80%, 85%, 90%, 95%, 98% or 99%. "Sequence identity" is the percentage of residues in an amino acid or nucleic acid sequence that are identical after aligning the sequence with a reference sequence and introducing gaps, if necessary, to achieve maximal sequence identity. Methods and computer programs for the alignment, such as BLAST, are well known in the art. For example, if a polypeptide is substantially identical with the 170 residues from the N terminus and 90 residues from the C terminus of a naturally occurring bacterial flagellin, then when the polypeptide and the reference sequence (170 residues from the N terminus and 90 residues from the C terminus of the naturally occurring bacterial flagellin) are maximally aligned, at least 30% of the amino acids in the reference sequence are found in the corresponding positions in the polypeptide. The term "substantially identical", at the cellular level, means that a cell is sufficiently similar to a cell of a host, such that the host's immune system does not mount an immune response against the substantially similar cell (i.e., the cell is recognized as a self cell by the immune system).

"Treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving the disease, i.e., causing regression of the state, disorder or condition or at least one of its clinical or subclinical symptoms.

The benefit to an individual to be treated is either statistically significant or at least perceptible to the patient or to the physician. In a specific embodiment of the invention, "treating a cancer" means alleviating or eliminating the symptoms of a tumor, or slowing down the progress of the tumor. The alleviating or eliminating effect can be determined by any method known in the art, such as measuring the size of the tumor and observing biochemical indicators of the particular tumor. For example, a subject is treated if showing one or more of the following: reduction in the number of cancer cells; reduction in the tumor size; inhibition or elimination of cancer cell infiltration into peripheral organs, including the spread of cancer into soft tissue and bone; inhibition or elimination of tumor metastasis; inhibition of tumor growth; reduction of one or more of the symptoms associated with the specific cancer; and reduced morbidity and mortality. The alleviation is preferably at least about 10%, more preferably at least about 20%, 30%, 40%, 50%, 60%, 70%, 80% or 90%.

As used herein, a "flagellin" may be may be any polypeptide that binds a naturally occurring TLR5 and triggers at least one of the biological functions of the TLR5 in antigen-presenting cells upon such binding. Thus, a flagellin may be a polypeptide comprising any of the naturally occurring bacterial flagellin proteins. A flagellin may also be a polypeptide that is substantially identical with any of the naturally occurring bacterial flagellin proteins at the amino acid sequence level, wherein the polypeptide is capable of binding a naturally occurring TLR5. Furthermore, a flagellin may be a polypeptide that is substantially identical with the 170 residues from the N terminus and 90 residues from the C terminus of any of the naturally occurring bacterial flagellin proteins at the amino acid sequence level, wherein the polypeptide is capable of binding a naturally occurring TLR5. The flagellin of this invention may also comprise a modification, such as glycosylation or phosphorylation. The flagellin may also be a mutant or protein variant of flagellin.

Flagella are found primarily, although not exclusively, on the surface of rod and spiral shaped bacteria, including members of the genera *Escherichia, Salmonella, Proteus, Pseudomonas, Bacillus, Campylobacter, Vibrio, Treponema, Legionella, Clostridia*, and *Caulobacter*. Flagellin sequences are readily obtainable based on knowledge in the art. In fact, the flagellin sequences from numerous bacterial species, as well as structural analyses, have been published. Any analogs, derivatives of flagellin or fragments thereof with flagellin function, namely one that binds a naturally occurring TLR5 and/or NLRs (Naip5 and/or Ipaf) and triggers at least one of the biological functions of TLR5 and/or Naip5 and/or Ipaf in antigen-presenting cells upon such binding, can be used in the present invention. These include polypeptides comprising any of the naturally occurring bacterial flagellin proteins, and polypeptides that are substantially identical with any of the naturally occurring bacterial flagellin proteins at the amino acid sequence level, wherein the polypeptides are capable of binding a naturally occurring TLR5 and/or Naip5 and/or Ipaf.

Flagellin sequences from numerous bacteria are available in the art, such as but not limited to GenBank accession numbers D13689 (nucleic acid sequence) (SEQ ID NO: 2), YP_275549 (SEQ ID NO: 3), YP_275550 (SEQ ID NO: 4), AAU18718 (SEQ ID NO: 5), AAU18717 (SEQ ID NO: 6), ZP_00743095 (SEQ ID NO: 7), EAO52626 (SEQ ID NO: 8), YP_315348 (SEQ ID NO: 9), AAT28337 (SEQ ID NO: 10), AAT28336 (SEQ ID NO: 11), AAT28335 (SEQ ID NO: 12), AAT28334 (SEQ ID NO: 13), AAT28333 (SEQ ID NO: 14), AAZ36356 (SEQ ID NO: 15), AAZ33167 (SEQ ID NO: 16), AAZ94424 (SEQ ID NO: 17), AAZ91670 (SEQ ID NO: 18), BAD18052 (SEQ ID NO: 19), and BAD18051 (SEQ ID NO: 20). Any suitable flagellin nucleic acid or amino acid sequence, or suitable fragment thereof, now known or to be later discovered is contemplated for use in the fusion proteins of the present invention.

The flagellin proteins from different species exhibit a high degree of protein sequence homology at the amino and carboxy termini (about 170 residues from the N terminus and about 90 residues from the C terminus), and the presence of a polymorphic central region which is responsible for the antigenic diversity among different flagella. The conserved regions are important for TLR5 binding, while the polymorphic central region can be deleted without affecting binding to TLR5. Structural-function analyses of the flagellin proteins have been reported (see, e.g., Smith K D et al., Toll-like receptor 5 recognizes a conserved site on flagellin required for protofilament formation and bacterial motility, Nat. Immunol. 2003 December; 4(12):1247-53; Murthy K G et al., Identification of conserved domains in *Salmonella muenchen* flagellin that are essential for its ability to activate TLR5 and to induce an inflammatory response in vitro, J Biol. Chem. 2004 Feb. 13; 279(7):5667-75; U.S. Pat. No. 6,130,082; and U.S. Patent Application Publication No. 2003/0044429). Thus, mutants or variants of flagellin, which maintain the TLR4 and/or NLR activating capacity are also contemplated for use in the present invention.

In a specific embodiment, a fusion protein of the invention comprises a TAA and a fragment of flagellin. In one embodiment, the fragment of flagellin is capable of binding to TLR5 but not Naip5 or Ipaf. For example, the Flagellin fragment can be missing the C-terminal portion required for NLR activation and contain a conserved sequence recognized by TLR5 [See Smith, K. D. et al. Nat Immunol 2003 vol. 4 (12) pp. 1247-53]. In a preferred embodiment, the fragment of flagellin is capable of binding to NLRs (e.g., Naip5 and Ipaf) but not to TLR5. For example, the C-terminal sequence of flagellin from *S. Typhimurium*: VLAQANQVPQNVLSLLR (SEQ ID NO: 31) or the sequence TSVLAQANQVPQNVLSLLR (SEQ ID NO: 32) may be comprised in a fusion protein of the invention. It is to be understood that this sequence can differ from one bacteria to another but the key residues for Ipaf and Naip5 activation are conserved [Karla L Lightfield, et al. Nat Immunol 2008 vol. 9 (10) pp. 1171-1178]. Thus variants of this sequence containing the conserved residues required by binding and activation of NLR are also contemplated for use in the instant invention.

In another embodiment, a fusion protein of the invention comprises the C-terminal sequence of flagellin from *S. typhimurium*: VLAQANQVPQNVLSLLR (SEQ ID NO: 31) or the sequence TSVLAQANQVPQNVLSLLR (SEQ ID NO: 32), (both of which can activate Naip5 or Ipaf but not TLR5) and the TLR ligand PLP. Thus, this fusion protein contains at least one TLR ligand and at least one NLR ligand. Another example of such a fusion protein is a fusion protein comprising PLP and a fragment of anthrax toxin (the amino acid sequence required for binding to NLR NLRP 1) or a fusion protein comprising PLP and a fragment of the *Staphylococcus aureus* alpha-hemolysin (the amino acid sequence required for binding to the NLR NLRP3).

In certain embodiments, an example of an amino acid sequence of flagellin which activates both TLR5 and NLR is a full length flagellin. In certain embodiments, an example of an amino acid sequence of flagellin which activates NLR but not TLR5 is TSVLAQANQVPQNVLSLLR (SEQ ID NO:

32). A sequence which activates TLR5 but not NLR is a flagellin amino acid sequence in which the last 20 residues at the C-terminus are deleted.

While the present Examples use flagellin-TAA fusion proteins, the invention is not to be limited thereto. Also contemplated by the present invention are fusion proteins comprising other TLR and/or NLR ligands and a TAA. Preferably, the TLR or NLR ligand is a polypeptide ligand, in order to facilitate its expression as a fusion protein, e.g, in tumor cell. For example, the protein TLR11 ligand, profilin-like protein (PLP), or a fragment thereof, for which amino acid sequences from many different organism are known, may also be used as a TLR ligand in a fusion protein of the present invention. Non-limiting examples of amino acid sequences of PLP, which may be used to generate a fusion protein of the invention include GenBank Accession numbers ABB43118 (SEQ ID NO: 21), BAB09877 (SEQ ID NO: 22), ABZ80128 (SEQ ID NO: 23), YP_717473 (SEQ ID NO: 24), ABD97732 (SEQ ID NO: 25), ABC61055 (SEQ ID NO: 26), ABB16985 (SEQ ID NO: 27), and AAY97753 (SEQ ID NO: 28). Anthrax toxin and *Staphylococcus aureus* toxins such as alpha-hemolysin (GenBank Accession no. AAA26598) (SEQ ID NO: 1) activate NLRP3 and are non-limiting examples of protein NLR ligands contemplated for use in the fusion proteins of the present invention.

Flagellin is unique in that is represents both a TLR (TLR5) and an NLR (Ipaf and Naip5) ligand. Thus, in a preferred embodiment of the invention, a fusion protein of the invention comprises a TAA and a ligand that stimulates both a TLR and an NLR. In another preferred embodiment of the invention, a fusion protein comprises a TAA and two or more TLR ligands, or two or more NLR ligands, or at least one TLR ligand and at least one NLR ligand. In a specific embodiment, a fusion protein of the invention comprises a TAA (e.g. MUC-1), PLP (a TLR ligand) and anthrax toxin (an NLR ligand). While not intending to be bound by any specific theory or mechanism, such a fusion protein expressed in a tumor cell is thought to be especially efficient for DC activation because it can trigger both TLR and NLR signaling. In another embodiment, a tumor cell of the invention may be engineered to express two or more fusion proteins, wherein at least one fusion protein comprises a TAA and a TLR ligand (e.g. PLP) and another at least one fusion protein comprises a TAA and an NLR ligand (e.g. anthrax toxin). The TAA in each construct expressed in the tumor may be the same TAA or a different TAA.

In certain embodiments of the invention, a mammalian cell, preferably a tumor cell, and still more preferably an autologous tumor cell, are engineered to express an NLR- or TLR-ligand-TAA fusion protein.

Tumor-associated antigens are well known and described in the art. Any protein antigen expressed by a tumor cell is contemplated for use in the present invention. Preferred TAAs are those which are known to be highly immunogenic (i.e., that comprise immunodominant epitopes that will stimulate a strong anti-tumor immune response.) Non-limiting examples of TAAs contemplated for use in the fusion proteins of the present invention include ErbB receptors, Melan A [MART1], gp100, tyrosinase, TRP-1/gp 75, and TRP-2 (in melanoma; for additional examples, see also a list of antigens provided in Storkus and Zarour, Forum (Genova), 2000 July-September, 10(3):256-270); MAGE-1 and MAGE-3 (in bladder, head and neck, and non-small cell carcinoma); HPV E6 and E7 proteins (in cervical cancer); Mucin [MUC-1] (in breast, pancreas, colon, and prostate cancers); prostate-specific antigen [PSA] (in prostate cancer); carcinoembryonic antigen [CEA] (in colon, breast, and gastrointestinal cancers), PIA tumor antigen (e.g., CTL epitope LPYLGWLVF (SEQ ID NO: 29) as disclosed in WO 98/56919), and such shared tumor-specific antigens as MAGE-2, MAGE-4, MAGE-6, MAGE-10, MAGE-12, BAGE-1, CAGE-1,2,8, CAGE-3 to 7, LAGE-1, NY-ESO-1/LAGE-2, NA-88, GnTV, and TRP2-INT2 a chimeric tumor CTL epitope string such as MLPYLGWLVF-AQHPNAELL-KHYLFRNL-SPSYVY-HQF-IPNPLLGLD (SEQ ID NO: 30) (see, e.g., PCT Application No. WO 98/56919). (Robson N C, Hoves S, Maraskovsky E, Schnurr M, Curr Opin Immunol. 2010 Jan. 28, Epub ahead of print).

Tumor cells may be isolated from a mammalian subject or patient. For example, a tumor may be removed from a patient during a biopsy or surgery, and tumor cells may be obtained and cultured from the biopsy sample [Liangping Li, Establishment of tumor cell lines by transient expression of immortalizing genes Gene Ther Mol Biol Vol 4, 261-274. December 1999]. Tumor cells may be autologous or non-autologous. Tumor cells for use in the instant invention may also be derived from any suitable tumor cell line. Non-limiting examples of tumor cell lines contemplated for use in the present invention include DU145 (Prostate cancer), Lncap (Prostate cancer), MCF-7 (breast cancer), MDA-MB-438 (breast cancer), PC3 (Prostate cancer), T47D (breast cancer), THP-1 (acute myeloid leukemia), BN1 (melanoma), U87 (glioblastoma), SHSY5Y Human neuroblastoma cells, cloned from a myeloma, and Saos-2 cells (bone cancer). Any suitable tumor cell line is contemplated for use in the present invention.

One or more fusion protein of the invention are expressed in tumor cells of the invention. Methods of expressing exogenous or recombinant proteins in a cell are well known in the art. Such methods include, but are not limited to, transfection, microinjection, scrape-loading, and receptor-mediated uptake by the cell. Transfection may be transient or stable. Exemplary current methods of transfection include calcium phosphate precipitation, electroporation, lipofection, and peptide-mediated transfection. Ballistic DNA delivery and transduction (i.e., the introduction of foreign DNA by virus or virus vector infection) can also be employed.

For example, a flagellin or other TLR or NLR ligand can be delivered to cells by means of an expression vector. Suitable expression vectors comprise a promoter that is active in the cells in which the ligand is to be expressed. Expression vectors useful for practicing the invention may also include selectable markers, cell-type or cell-cycle-specific enhancers or repressors, polylinkers, start codons, ribosome binding sites, internal ribosome entry sites, introns, stop codons, polyadenylation signals, or other features that facilitate cloning and vector stability, mRNA stability and localization in the cell, and translation efficiency, or combinations thereof. Expression vectors include viral expression vectors. Selection of these features is largely based on the cells to be transfected, and the expression characteristics desired. A large number of commercially available vectors are available for expressing polypeptides in cells.

Also contemplated by the present invention are modified fusion proteins, such as glycosylated or phosphorylated fusion proteins. Subcellular targeting motifs are also contemplated.

Methods for cloning expression vectors (fusion protein constructs), and methods for expressing and purifying recombinant fusion proteins of the invention are described in detail in Juleatt J. W. et al (2007) Vaccine (25)763-775. For example, vectors may also be expressed in tumor cells using retroviral, adenoviral or lentiviral vectors.

Tumor cells for use in the present invention may be apoptotic or live (non-apoptotic) cells. Preferably, apoptosis is induced in tumor cells just prior to incubation with DCs or prior to administration to a subject. This may be done in order to prevent proliferation of tumor cells in the recipient. Further, while not intending to be bound by any particular theory or mechanism, apoptotic cells are easily recognized by DC and internalized. Internalization delivers the apoptotic cell and all proteins derived thereof into endo-lysosomal compartments that generate the ligands necessary for the activation of $CD4^+$ and $CD8^+$ T cells. When a DC internalizes an apoptotic cell that was made to express a TLR ligand-TAA or NLR-ligand TAA fusion protein, this DC will additionally become activated and induce a potent adaptive immune response. Such activation does not occur if a DC internalizes an apoptotic cell lacking the expression of the TLR or NLR ligand. Expression of a TAA alone by an apoptotic cell and in the absence of the TLR or NLR ligand will not activate the DC [Blander, J. M. and Medzhitov, R., Nature (2006), Vol. 440, pp. 808].

Apoptosis may be induced using chemotherapeutic agents (such as, e.g., oxaliplatin, cisplatin, carboplatin or other platinum-based drugs), alkylating agents (e.g., mitomycin C), toposiomerase II inhibitor (e.g., etoposide) anthracyclins (e.g., mitoxantrone), inducers of endoplasmic reticulum stress (e.g., thapsigargin), or cells may be lethally irradiated. A cell is "lethally irradiated" if the cell, after the irradiation, is not capable of replicating (i.e., dividing into two or more cells). Art-recognized methods can be used to determine the dose of radiation and whether the irradiated cells can replicate. For example, cells growing at a density of $5 \times 10^5$ cells/ml can be irradiated with 10,000 Rads, then viable cell numbers can be determined over time by, e.g., Trypan blue exclusion. To be useful in the present invention, the lethally irradiated cell should preferably be able to continue to express proteins for a period of time (see, e.g., Borrello I et al., A universal granulocyte-macrophage colony-stimulating factor-producing bystander cell line for use in the formulation of autologous tumor cell-based vaccines, Hum Gene Ther. 1999 Aug. 10; 10(12):1983-1991). Protein expression by the lethally irradiated cells can be assayed by methods known in the art, such as gel electrophoresis and protein staining for protein synthesis in general, or Western analysis for specific protein(s).

In certain embodiments of the invention, methods for inducing an anti-tumor immune response in a mammal or for treating a cancer are provided, with methods comprise administering to a mammal or patient an immunogenically effective amount of a composition comprising a DC, wherein the DC has internalized a tumor cell expressing a fusion protein if the invention. DCs are known to be potent stimulators of the adaptive immune response (e.g. T and/or B cell mediated immune responses).

Several clinical trials for anti-tumor immunotherapy are based on the use of dendritic cells (DC) loaded with tumor cell extracts [reviewed in Koski et al. (2008), supra]. In such protocols, TLR ligands could be used in order to ensure the proper maturation of DC prior to injection into patients. While such strategies are promising, their efficacy is still poor. In conjunction with the present discovery that tumor cells expressing TLR- and/or NLR-ligand-TAA fusion protein are superiorly immunogenic, and facilitate tailoring of a highly antigen-specific immune response to the desired TAA, the present invention provides methods for achieving superior efficacy of DC-based immunotherapies.

Specifically, the present invention is based in part on the results of immunizing mice with dendritic cells loaded with tumor cells expressing TLR- or NLR-ligand-TAA fusion protein compared to immunizing mice with DCs loaded with tumor cells and TLR ligand and TAA separately. While not intending to be bound by any particular theory or mechanism, it is believe that the superiority of the methods and compositions of the instant invention is achieved because the physical linkage in a fusion protein of the TAA to the TLR or NLR ligand (PAMP) facilitates delivery of both the activation signal (PAMP) and the antigen (TAA) to the same endo/lysosomal compartment within the DC, thereby increasing DC activation and the ability to induce a potent, antigen-specific immune response to the TAA. Furthermore in addition to inducing a specific immune response to the TAA, the tumor cell provides additional antigens that also contribute to the development of a potent anti-tumor immune response of superior quality to presently available methods.

In other embodiments, tumor cells for direct immunization of patients may be dead tumor cells expressing a fusion protein of the invention. Tumor cells can be rendered dead by various means such as irradiation or as indicated above. It may be confirmed that tumor cells are dead by propidium iodide incorporation, TUNEL assay, Annexin-V and 7-Aminoactinomycin D (7AAD) or any other suitable method known in the art. Tumor cells may also be necrotic.

According to the methods of the present invention, human DC precursors (i.e. circulating monocytes), preferably obtained from the tumor-bearing patient to be treated (i.e. autologous cells), can be isolated and differentiated overnight ex vivo into DCs using a well-defined protocol that involves culture in the cytokines IL-4 and GM-CSF [(Gilliet, M. F. and F. O. Nestle Methods in Mol Med 2001, 10.1385/1-59259-150-7:297; Sallusto, F. and Lanzavecchia, A. (1994). *J. Exp. Med.* 179, 1109-1118; Romani, N., Gruner, S., Brang, D., Kampgen, E., Lenz, A., Trockenbacher, B., Konwalinka, G., Fritsch, P. O., Steinman, R. M., and Schuler, G. (1994) *J. Exp. Med.* 180, 83-93). DC can be subsequently pulsed for, e.g., 6 hours with tumor cell extracts (γ-irradiated tumor cell for example) that had been previously engineered to express the TLR5 and/or Ipaf and/or Naip5 ligand flagellin fused to a tumor associated antigen of choice (different strategies will be evaluated: retroviral-based gene transfer, adenoviral gene transfer or transfection). It is also possible to pulse the DCs with whole tumor suspensions that have or have not been irradiated or induced to become apoptotic or necrotic Optionally, IFN-γ or other inflammatory cytokine such as TNF-α, or antibodies to the co-stimulatory molecule CD40 (anti-CD40), are added to the culture to increase the maturation (e.g., upregulation of costimulatory molecules) of DC prior to the injection.

Flagellin-TAA fusion protein expressing-tumor "loaded" DCs (i.e., DCs that have internalized tumor cells or tumor cell extract) can be injected into the patient via different routes, e.g., intravenously, subcutaneously or directly into the tumor-draining lymph node. Any suitable route of injection is contemplated by the present invention. Direct injection into a tumor-draining lymph node can ensure the proximity of the DC to T cells in order to induce an antigen-specific T cell driven immune response. The number of loaded DCs to be injected as well as the frequency of injection can be determined experimentally. Clinical criteria for evaluating efficacy of immunotherapies are well defined, in particular for solid tumor (J. D Wolchok, A Hoos, S O' day, J. S Weber, O Hamid, C Lebbe, M Maio, M Binder, O Bohnsack, G Nichol, R Humphrey, F. S Hodi. Clinical Cancer Research, 2009 vol. 15 (23) pp. 7412-7420). Thus, efficacy of the DC-based therapies of the invention may follow these criteria.

One advantage of the present invention is that the compositions for use in the present methods may be specifically tailored to a patient. For example, in a specific embodiment, tumor cells for preparing a composition of the invention may be obtained from the same patient who is to be administered the composition (i.e., the tumor cells may be autologous to the cells of the patient). Autologous tumor cells are preferred as they express the same antigens expressed by the patient's tumor cells, and will thus help drive an effective anti-tumor immune response directed against the patient's tumor, by allowing generation of immune response against additional antigens (in addition to the TAA). Non-autologous tumor cells may also be used however, since they are engineered to express a TAA-containing fusion protein, wherein the TAA is preferably expressed by the patient's tumor cells.

Similarly, DCs may be autologous cells. This is preferred, since self DCs will not stimulate an alloimmune response, and will therefore avoid being eliminated by the host immune system before inducing the anti-tumor immune response.

Compositions and Uses

In a specific embodiment of the invention, a composition comprises a tumor cell expressing a fusion protein, wherein said fusion protein comprises a TLR ligand and/or an NLR ligand and a TAA. In a preferred embodiment, a composition of the invention comprises a DC, wherein the DC has internalized a tumor cell expressing a fusion protein comprising a TLR ligand and/or NLR ligand and a tumor-associated antigen (TAA). In other words the DC is "loaded" with a fusion-protein expressing tumor cell. Optionally, the loaded DC has been treated with IFN-γ before administration to the patient. Furthermore, the tumor cell with which the DC is loaded may be lethally irradiated and/or apoptotic or necrotic. In some embodiments, the DC is loaded with extracts from a tumor cell expressing a fusion protein of the invention.

The compositions and methods of the present invention are useful for inducing an anti-tumor immune response, and for cancers. Examples of cancer include, but are not limited to, carcinoma, lymphoma, blastoma, sarcoma, and leukemia or lymphoid malignancies. More particular examples of cancers include: squamous cell cancer (e.g., epithelial squamous cell cancer), lung cancer (including small-cell lung cancer, non-small cell lung cancer, adenocarcinoma of the lung and squamous carcinoma of the lung), cancer of the peritoneum, hepatocellular cancer, gastric or stomach cancer (including gastrointestinal cancer, pancreatic cancer), glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. A cancer includes primary malignant cells (e.g., those that have not migrated to sites in the subject's body other than the site of the original malignancy) and secondary malignant cells (e.g., those arising from metastasis, the migration of malignant cells to secondary sites that are different from the site of the original tumor).

Pharmaceutical Compositions and Administration

While it is possible to use a composition provided by the present invention for therapy as is, it may be preferable to administer it in a pharmaceutical formulation, e.g., in admixture with a suitable pharmaceutical excipient, diluent, or carrier selected with regard to the intended route of administration and standard pharmaceutical practice. Accordingly, in one aspect, the present invention provides a pharmaceutical composition or formulation comprising at least one composition of the invention, or a pharmaceutically acceptable derivative thereof, in association with a pharmaceutically acceptable excipient, diluent, and/or carrier. The excipient, diluent and/or carrier must be "acceptable" in the sense of being compatible with the other ingredients of the formulation and not deleterious to the recipient thereof.

The compositions of the invention can be formulated for administration in any convenient way for use in human or veterinary medicine.

Pharmaceutical Carrier

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E.W. Martin (1990, Mack Publishing Co., Easton, Pa. 18042).

Vaccines

The term "vaccine" refers to a composition that can be used to elicit protective immunity in a recipient. It should be noted that to be effective, a vaccine of the invention can elicit immunity in a portion of the immunized population, as some individuals may fail to mount a robust or protective immune response, or, in some cases, any immune response. This inability may stem from the individual's genetic background or because of an immunodeficiency condition (either acquired or congenital) or immunosuppression (e.g., due to treatment with chemotherapy or use of immunosuppressive drugs). Vaccine efficacy can be established in animal models.

Formulations

The compositions and formulations of the present invention may comprise pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. See, e.g., Remington's Pharmaceutical Sciences, 18th Ed. (1990, Mack Publishing Co., Easton, Pa. 18042) pages 1435 1712 which are herein incorporated by reference.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants, preserving, wetting, emulsifying, and dispersing agents. The pharmaceutical compositions may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Administration and Dosage

The compositions (e.g., pharmaceutical or vaccine compositions) and formulations of the present invention can be administered parenterally, by inhalation, or by other suitable methods known in the art. The term "parenteral" includes injection (for example, intravenous, intraperitoneal, epidural, intrathecal, intramuscular, intraluminal, intratracheal or subcutaneous). Injections directly into the primary site of tumor are also contemplated. The preferred routes of administration are subcutaneous and intravenous and direct injection into a tumor-draining lymph node.

The compositions and formulations of the present invention may be administered to an animal, preferably a mammal, and most preferably a human.

The dosage of the compositions or formulations of the present invention will vary widely, depending upon the nature of the disease, the patient's medical history, age, body weight, sex, sensitivity, the frequency of administration, the manner and route of administration, the clearance of the agent from the host, dosage period, drugs used in combination, and the like. The initial dose may be larger, followed by smaller maintenance doses.

For any composition or formulation used in the methods of the invention, the therapeutically effective dose can be estimated initially from animal models. Dose-response curves derived from animal systems are then used to determine testing doses for the initial clinical studies in humans. In safety determinations for each composition, the dose and frequency of administration should meet or exceed those anticipated for use in the clinical studies.

The data obtained from the animal studies can be used in formulating a range of doses for use in humans. The therapeutically effective doses of in humans lay preferably within a range of circulating concentrations that include the $ED_{50}$ with little or no toxicity. The dosage can vary within this range depending upon the dosage form employed and the route of administration utilized. Ideally, a single dose of each drug should be used daily.

The compositions of the invention will typically contain an effective amount of the compositions for achieving the desired effect. The term "therapeutically effective amount/dose" is used interchangeably with the terms "immunogenically effective amount/dose" and "effective amount/dose" and refers to an amount of the substance that is sufficient to achieve the intended effect. An immunogenically effective amount of a flagellin-TAA-expressing tumor cell of the invention is an amount of the cell that is sufficient to induce an anti-tumor immune response. An effective amount of a composition (e.g. vaccine) for inducing an anti-tumor immune response is an amount of the composition sufficient to alleviate or eliminate the symptoms of the tumor, for slowing down the progress of the tumor, for eliminating or reducing the size of the tumor, or for preventing the development of a tumor and metastases. The effective amount will vary with factors such as the nature of the substance, the route of administration, the formulation comprising the substance, and the size, species, and health condition of the recipient of the substance. Methods to determine the effective amount are known in the art.

Administration of the compositions or formulations of the invention may be once a day, twice a day, or more often, but frequency may be decreased during a maintenance phase of the disease or disorder, e.g., once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art. More generally, dose and frequency will depend in part on recession of pathological signs and clinical and subclinical symptoms of a disease, condition or disorder contemplated for treatment with the present compounds.

The appropriate dose and dosage times under certain conditions can be determined by the test based on the above-described indices but may be refined and ultimately decided according to the judgment of the practitioner and each patient's circumstances (age, general condition, severity of symptoms, sex, etc.) according to standard clinical techniques.

Keeping the above description in mind, typical dosages of DCs in a composition of the invention range from about $1\times10^6$ to about $10\times10^7$ cells. However more or fewer DCs may be used.

Keeping the above description in mind, typical dosages of tumor cells in a composition of the invention range from about $1\times10^6$ to about $10\times10^7$ cells. However more or fewer tumor cells may also be used with similar results.

In certain embodiments, the present invention contemplates combination therapies. For example, in addition to treatment with a composition of the instant invention, a subject or patient having a tumor (such as a malignant tumor) may also be simultaneously, immediately before, or immediately after, subjected to another therapeutic measure such as but not limited to radiotherapy, chemotherapy or surgery. Another possible combination is to administer a composition of the present invention in combination with a humanized anti-CD25 antibody (Daclizumab) that depletes regulatory T cells. Regulatory T cells have been shown to be increased in number in the peripheral blood as well as tumors of patients with cancer, and can suppress the functions of anti-tumor effector CD4 and CD8 T cells. There are many other types of monoclonal antibody therapies that could be used in conjunction with (see, Dougan, M. and Dranoff, G. Ann Rev Immunol 2009, 27:4.1). These therapies include antibodies to EGFR (cetuximab and panitumumab), the related protein HER2/neu (transtuzumab), VEGF (Bevacizumab), or antibodies that are directed against surface proteins that are highly expressed on tumor cells, such as rituximab, alemtuzumab, gentuzumab, etc. Additionally, other TLR ligands such as various CpG derivatives or TLR7/TLR8 agonists such as Imiquimod, may be administered simultaneously within the formulation to enhance adjuvanticity of the preparations.

In accordance with the present invention, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press: Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press: Oxford; Freshney (2000) Culture of Animal Cells: A Manual of Basic Technique. 4th ed. Wiley-Liss; among others. The Current Protocols listed above are updated several times every year.

EXAMPLES

The present invention is described further below in working examples which are intended to further describe the invention without limiting the scope therein.

Example 1

Tumor Cells Expressing a TLR5/Ipaf/Naip5 Ligand Failed to Form a Tumor In Vivo

EL4 thymoma cells engineered to express either an ovalbumin (OVA) construct or an OVA-*S. typhimurium* flagellin fusion protein (STFOVA) using retroviral transduction with pMIG-IRES-GFP were subcutaneously injected in the flank into age and sex-matched syngeneic C57BL/6 (FIG. 1A) or MyD88$^{-/-}$ (FIG. 1B) mice in presence or not of recombinant flagellin (RecFLA, InvivoGen, San Diego, Calif.) (for wt only). Tumor progression was monitored by bi-weekly measure of tumor volume.

Figure 1B:
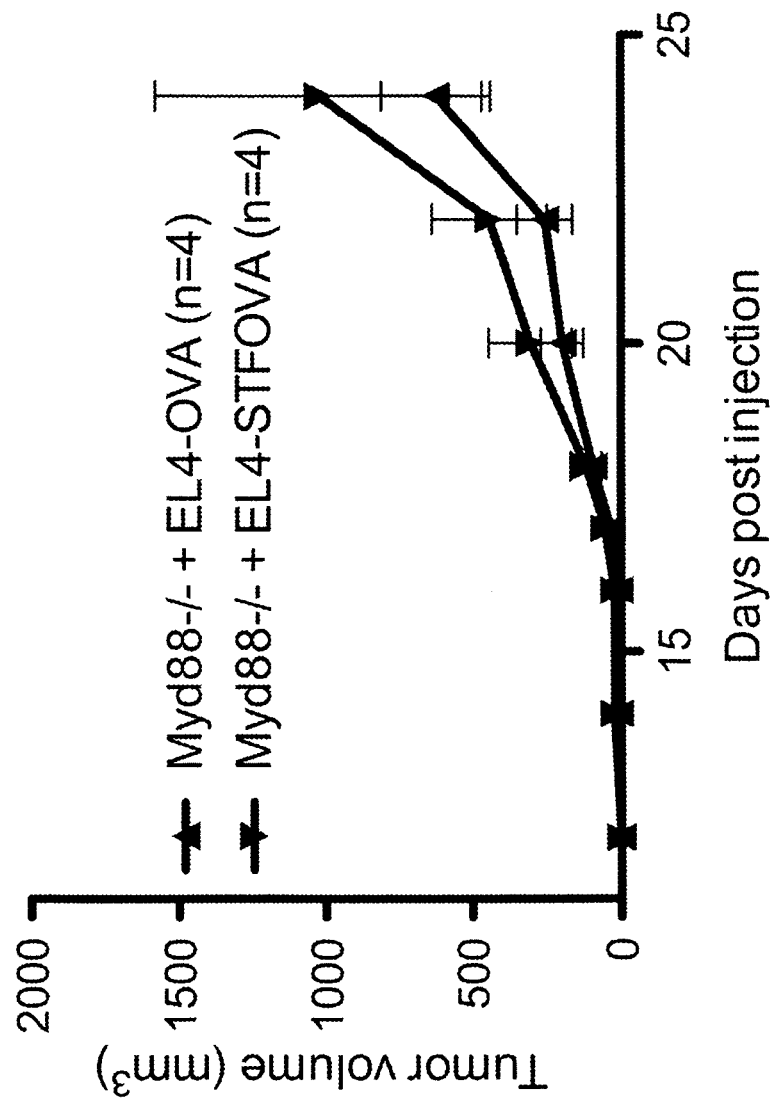
FIG. 1B is a graph showing a time course (days post injection) of tumor volume ($mm^3$) in MyD88 knockout ($Myd88^{-/-}$) mice injected with $1 \times 10^5$ EL4 thymoma cells engineered to express either an ovalbumin (OVA) construct or an OVA-*S. typhimurium* flagellin fusion protein (STFOVA) using retroviral transduction with pMIG-IRES-GFP.
Figure 9:
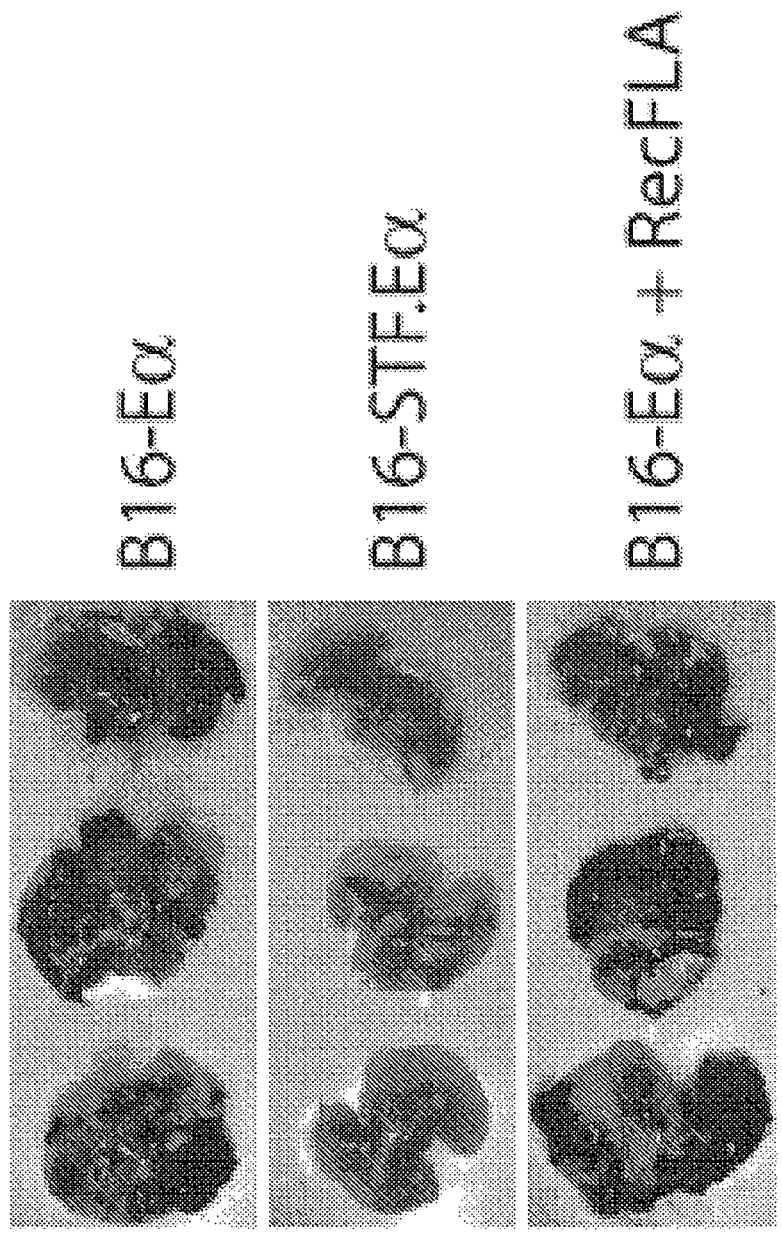
FIG. 9 shows pictures of lungs (3 mice per group) isolated at day 28 from wt mice injected with 100 000 B16 melanoma cells expressing Eα or Eα fused to flagellin (Stf.Eα). In another group, Eα expressing B16 cells were co-injected with 2 ng recombinant flagellin (RecFLA). B16 metastases are visualized as black foci.

The data show that the murine tumor cell lines EL4 (thymoma cell line) modified to express a flagellin-OVA fusion protein failed to establish tumors while EL4 cells expressing OVA grew normally (FIG. 1A). Importantly, the concomitant injection of recombinant flagellin (RecFLA) did not prevent EL4-OVA growth in vivo showing that introduction of the flagellin into tumors is critical for tumor rejection. Similar results were obtained using B16 melanoma cells expressing Ea as a tumor-associated antigen (FIG. 9). TLR5 signaling is entirely dependent on the MyD88 adaptor protein. Indeed, EL4-STFOVA transplanted into Myd88$^{-/-}$ mice successfully developed into palpable tumors (FIG. 1B). Because no difference was observed in vitro between proliferation of TLR modified cells and control cells, it was concluded that the immune system was responsible for the efficient elimination of TLR ligand modified tumors in vivo.

Example 2

Flagellin Induced Anti-Tumor Immunity Requires Lymphocytes $1\times10^5$ EL4 cells expressing OVA constructs were subcutaneously injected into the flank of Rag$^{-/-}$ or wt control mice. Tumor progression was monitored by bi-weekly measure of tumor volume.

Figure 2:
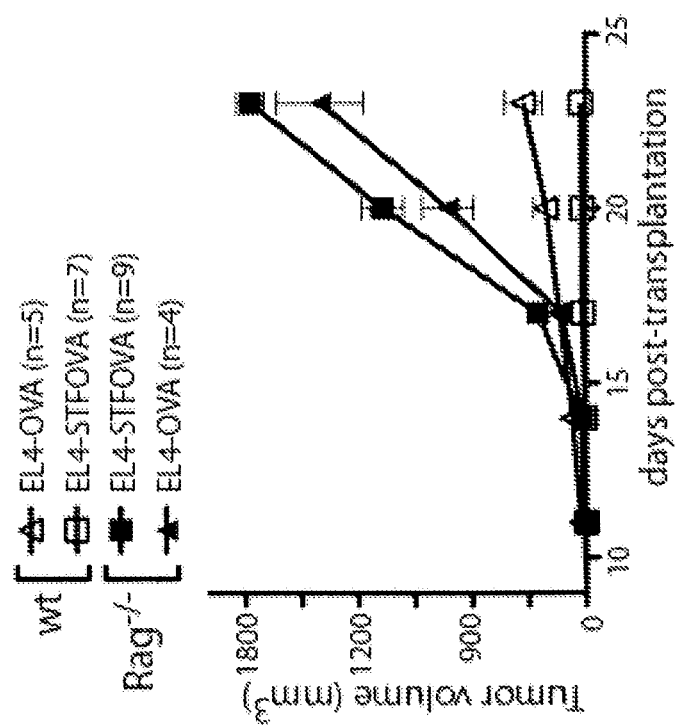
FIG. 2 is a graph showing a time course (days post-transplantation) of tumor volume ($mm^3$) in wild-type (wt) or $Rag^{-/-}$ mice transplanted with $1 \times 10^5$ EL4-OVA or EL4-STFOVA tumor cells.

The role of the adaptive immune system in the rejection of EL4-STFOVA when transplanted subcutaneously was evaluated. Rag$^{-/-}$ mice, which lack T and B lymphocytes, injected with EL4-STFOVA cells, allowed tumor progression while control wild type (wt) mice efficiently rejected the flagellin$^+$ tumor (FIG. 2). These results, together with the fact that EL4-STFOVA cells were able to form tumor in CD11c$^+$ DC-depleted mice, suggested that the innate immune system could efficiently initiate a TAA-specific adaptive immune response when tumor cells were internalized together with a TLR ligand into the same phagosome.

Example 3

Figure 3A:
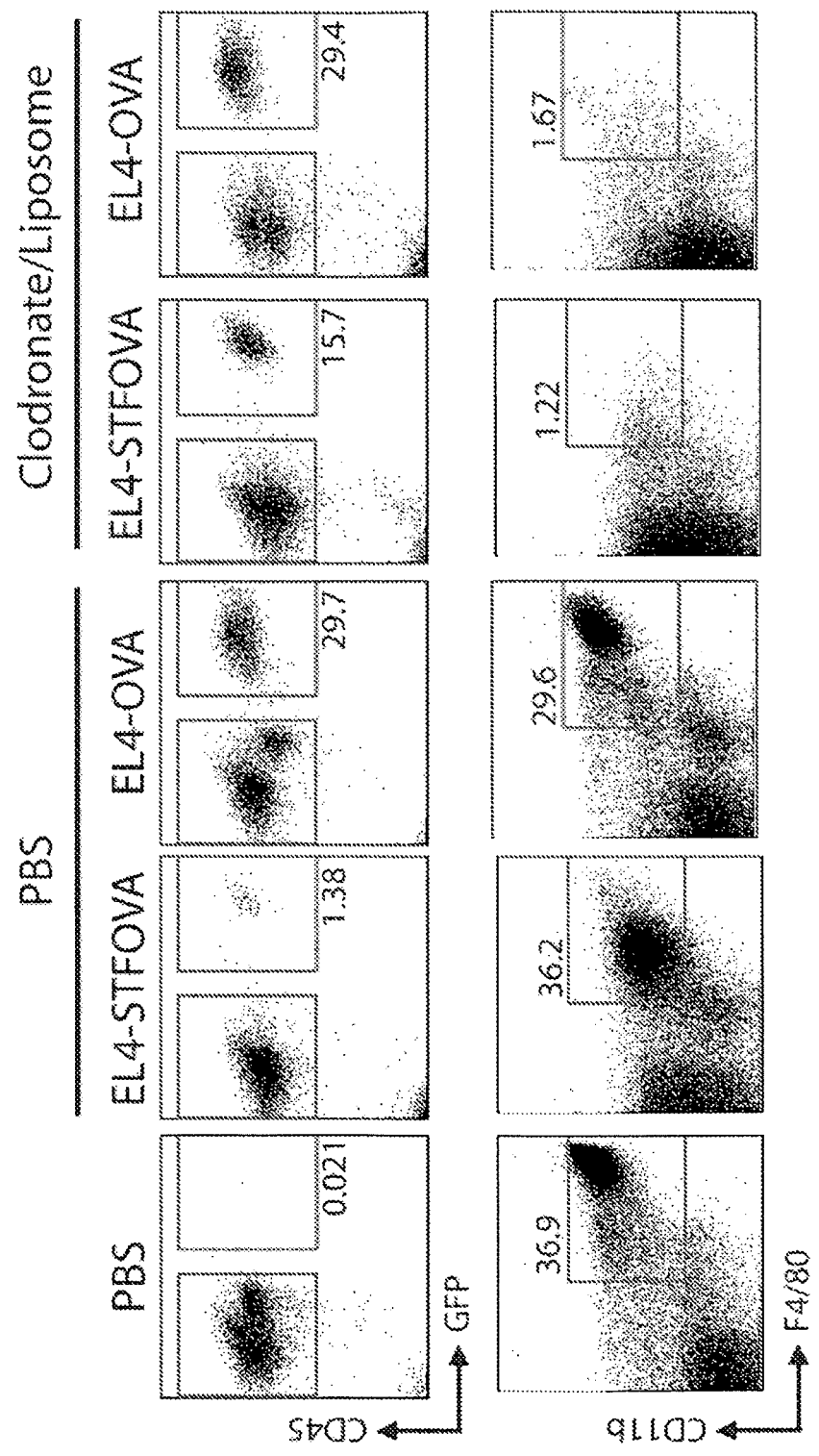
FIG. 3A shows two panels of flow cytometry dot plots showing peritoneal cells immunostained at 16 hours for CD45, F4/80, and CD11b in the indicated groups of mice, immunized with PBS, EL4-STFOVA or EL4-OVA, and treated with PBS or clodronate/liposome. The upper panel shows cells stained for CD45. Tumor cells are $CD45^+$ $GFP^+$ cells. The lower panel of dot plots shows CD11b and F4/80 stained cells. Macrophages are $CD11b^+$ $F4/80^+$ cells.
Figure 3B:
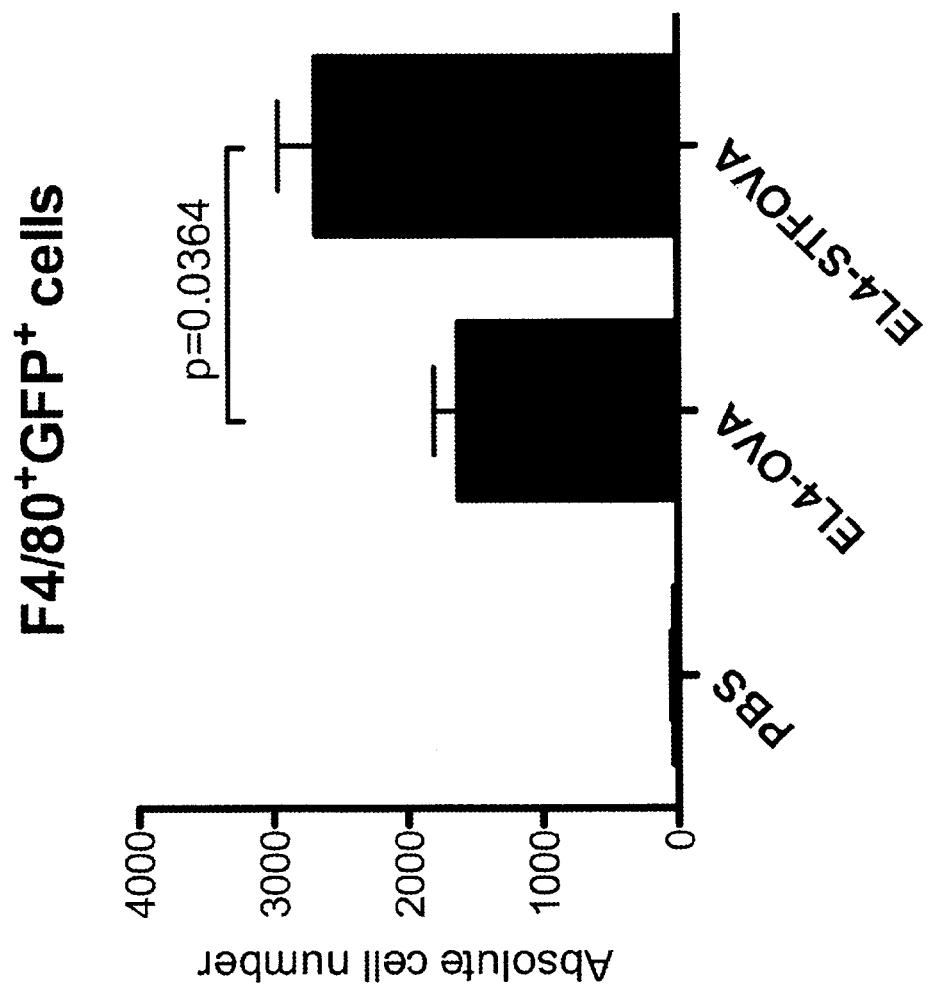
FIG. 3B is a graph quantifying the absolute cell number of peritoneal macrophages in the indicated groups (PBS, EL4-OVA and EL4-STFOVA immunized mice) containing tumor cells, 16 h after tumor cells were injected. Statistical significance is indicated (p=0.0364).

Tumor Cells Expressing a TLR5/Ipaf/Naip5 Ligand are Efficiently Targeted by the Innate Immune System Wild-type (wt) syngenic mice were injected intra-peritoneally with $3\times10^6$ EL4 cells expressing OVA or STFOVA. In FIG. 3A, flow cytometry dot plots show peritoneal cells immunostained at 16 hours for F4/80, CD11b (antibodies are from eBioscience, San Diego, Calif.). Tumor cells were CD45$^+$ GFP$^+$ cells. PBS injections served as a negative control. In FIG. 3B, the absolute cell number of macrophages containing tumor cells as measured by F4/80$^+$ GFP$^+$ cells in the peritoneal cavity 16 h after tumor cells were injected.

By injecting tumor cells expressing STFOVA in the peritoneal cavity, a site where a high number of innate immune cells (e.g. macrophages CD 11b$^+$ F4/80$^+$) is detected, the role of the innate immune system in response to a TLR5/Ipaf/Naip5 ligand bearing tumor cell was assessed. The importance of phagocytes was revealed by the use of clodronate/liposome (The foundation 'Clodronate Liposomes', The Netherlands), a reagent allowing specific depletion of these cells. In absence of macrophages, STFOVA expressing cells were detected in the peritoneum of mice treated with clodronate/liposomes while they were efficiently eliminated in control mice. Consistent with this finding, a higher number of macrophages (F4/80$^+$ cells) that have engulfed tumor cells was found in the peritoneal cavity of wt mice when tumor cells expressed the flagellin (FIG. 3B).

Example 4

Figure 4:
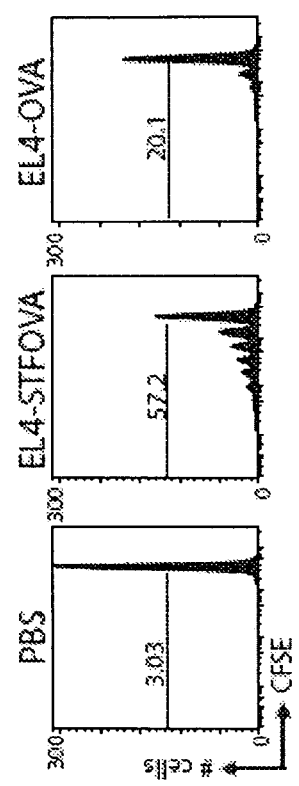
FIG. 4 is a dot plot showing proliferation of CFSE-labeled OVA-specific OT-II transgenic CD4⁺ T cells in tumor-draining lymph nodes at day 5 after tumor transplantation. Cells were stained with Thy1.2 and CD4 for analysis. The percentage of proliferating cells, demonstrated as cells with lower CFSE fluorescence intensity, in each of the indicated groups is shown.

Flagellin Induces In Vivo Priming of Tumor-associated Antigen Specific CD4$^+$ T Cells To test whether flagellin induces in vivo priming of tumor-associated antigen specific CD4$^+$ T cells directly, carboxyfluorescein diacetate succinimidyl ester (CFSE)$^+$OT-II CD4$^+$ T cell proliferation in tumor-draining lymph nodes five days after subcutaneous injection of EL4-STFOVA cells was monitored (FIG. 4).

Whether the presence of the TLR5 ligand flagellin within OVA-expressing tumors could induce OVA-specific OT-II CD4$^+$ T cells in vivo was investigated. It was found that expression of flagellin within tumor cells strongly enhanced TAA-specific CD4$^+$ T cell proliferation in vivo (FIG. 4). This finding is consistent with the previous observations demonstrating that TLR ligands enhance presentation of phagocytosed antigens within major histocompatibility class II MHC class II molecules [Blander, J. M. and Medzhitov, R., Nature (2006), Vol. 440, pp. 808]. These data also demonstrate that unlike EL4-OVA tumor cells, EL4-STFOVA tumor cells are capable of eliciting a helper anti-tumor CD4 T cell response.

Example 5

Figure 5A:
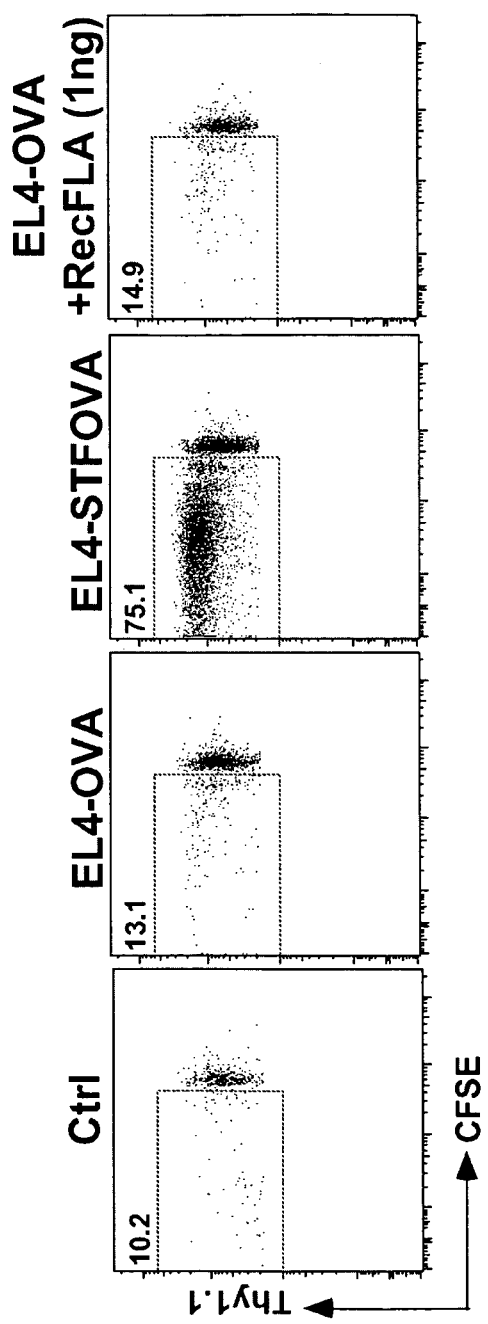
FIG. 5A is a panel of flow cytometry dot plots showing proliferation of OVA-specific CD8⁺ OT-I T cells in tumor draining lymph node at day 3 after tumor transplantation. Cells were stained with Thy1.1 for analysis. The percentage of proliferating cells (boxed cells) in each of the indicated groups is shown. In the EL4-OVA+RecFLA group, at the time of tumor injection, mice received a concomitant injection of 1 ng recombinant flagellin (RecFLA).
Figure 5B:
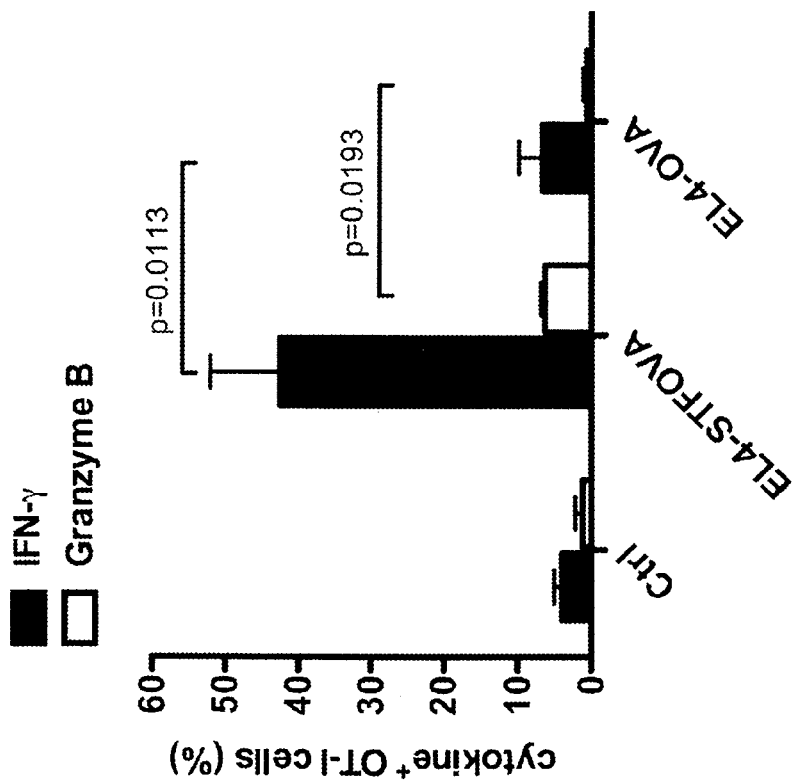
FIG. 5B is a graph showing the percentage (%) of IFN-γ and granzyme-B producing CD8⁺ OT-1 T cells (from FIG. 5A) measured by intracellular cytokine staining. Statistical significance (p value) is indicated on the graph.
Figure 5C:
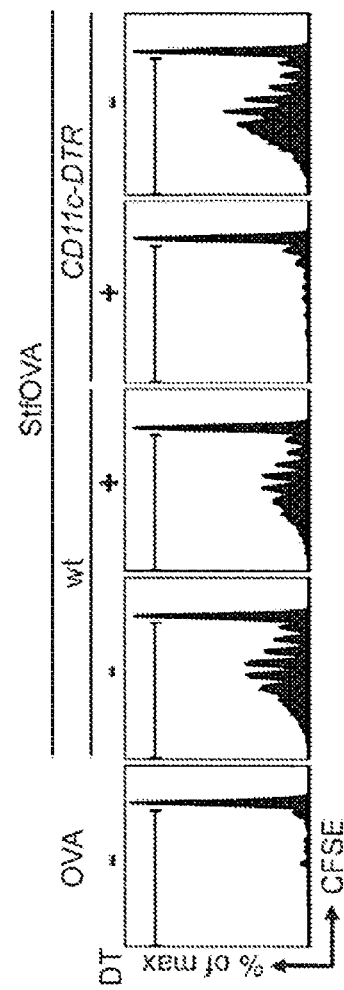
FIG. 5C is a panel of flow cytometry histograms showing proliferation of OVA-specific CD8⁺ OT-I T cells in tumor draining lymph node at day 3 after tumor transplantation in wild-type (wt) mice or CD11c-DTR mice treated (+) or not (−) with 2 injections of 100 ng diphtheria toxin (DT) to deplete DC. CD11c-DTR mice express DTR, an abbreviation for diptheria toxin receptor, driven by the CD11c promoter; Cells were stained with Thy1.1 and CD8 for analysis. $1 \times 10^5$ EL4 thymoma expressing OVA or STFOVA were transplanted.

Flagellin Induces In Vivo Cross-Priming of Tumor-associated Antigen Specific CD8$^+$ T Cells To test whether flagellin induces in vivo cross-priming of tumor-associated antigen specific CD8$^+$ T cells directly, carboxyfluorescein diacetate succinimidyl ester (CFSE)$^+$OT-1 CD8$^+$ T cell proliferation in tumor-draining lymph nodes three days after subcutaneous injection of EL4-STFOVA cells was monitored. Massive OT-1 T cell proliferation was induced in response to EL4-STFOVA expressing tumor cells but not in OVA-expressing tumor cells (EL4-OVA) or in EL4-OVA+recombinant Flagellin (RecFLA), showing that the presence of fusion protein physically lining the TLR ligand and the antigen within the tumor cells facilitated TAA crosspresentation (FIG. 5A). Moreover, interferon-γ and granzyme B secretion by TAA-specific CD8$^+$ T cells were enhanced in response to STFOVA expressing tumor cells compared to the other groups (FIG. 5B). Similar results were also obtained in vitro. In addition, a crucial role for DC in activation of CD8$^+$ T cells was observed because depletion of CD11c+ DC from the tumor bearing mice impaired the ability of CD8+ T cells to proliferate (FIG. 5C).

Taken together, the results of Examples 4 and 5 show that phagocytosis of flagellin+ fusion protein expressing tumor cells by DCs not only led to better CD8+ T cell activation, but also provided a critical signal for CD4+ T cell activation. Importantly, this effect was not observed when recombinant flagellin was co-injected (not as a fusion protein) with the EL4-OVA cells (FIG. 4) supporting the notion that the fusion protein containing the ligand for TLR5/Ipaf/Naip5 should be expressed by the tumor cells in order to induce a strong activation of the adaptive immune system.

Example 6

Figure 6A:
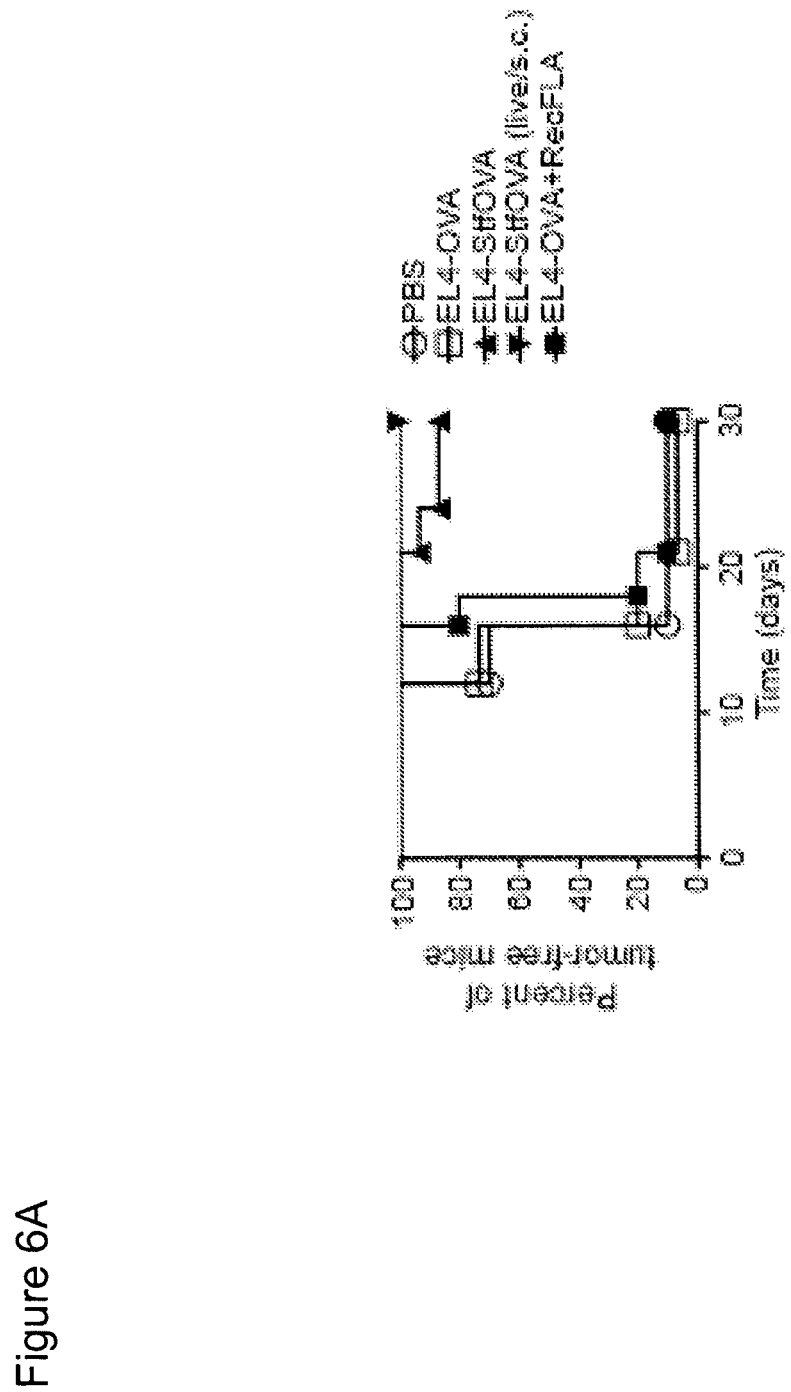
FIG. 6A is a graph showing a time course of the percentage (%) of tumor-bearing mice vaccinated in the flank with the indicated compositions (PBS (control), irradiated EL4-OVA tumor cells, irradiated EL4-STFOVA tumor cells, irradiated EL4-OVA tumor cells+2 ng RecFLA, or live EL4-STFOVA cells) 30 days after challenge with 50,000 live EL4-OVA cells in the opposite flank. "live" means non-irradiated tumor cells). Groups are composed of 10 mice.

Tumor Cells Expressing a TLR5/Ipaf/Naip5 Ligand Induce a Memory Anti-Tumor Response To test whether the injection of flagellin+ tumor cells expressing the STFOVA fusion protein could confer protective antigen-specific anti-tumor immunity, wild-type mice were vaccinated in the flank with the indicated compositions (PBS (control), 100,000 γ-irradiated EL4-OVA tumor cells, γ-irradiated EL4-STFOVA tumor cells, γ-irradiated EL4-OVA tumor cells+2 ng RecFLA, or live EL4-STFOVA cells). 30 days after vaccination, mice were challenged with 50,000 live EL4-OVA cells in the opposite flank ("live" means non-irradiated tumor cells) and tumor progression was measured as described above. Mice treated with irradiated or live flagellin fusion protein expressing tumor cells (EL4-STFOVA or EL4-STFOVA (live), respectively) were protected from a subsequent challenge with EL4-OVA. Only twenty percent of the mice 'vaccinated' with irradiated EL4-STFOVA and none of the mice treated with live EL4-STFOVA developed a tumor when challenged with EL4-OVA compared to eighty percent in the control groups (PBS or EL4-OVA vaccinated) (FIG. 6A).

Figure 6B:
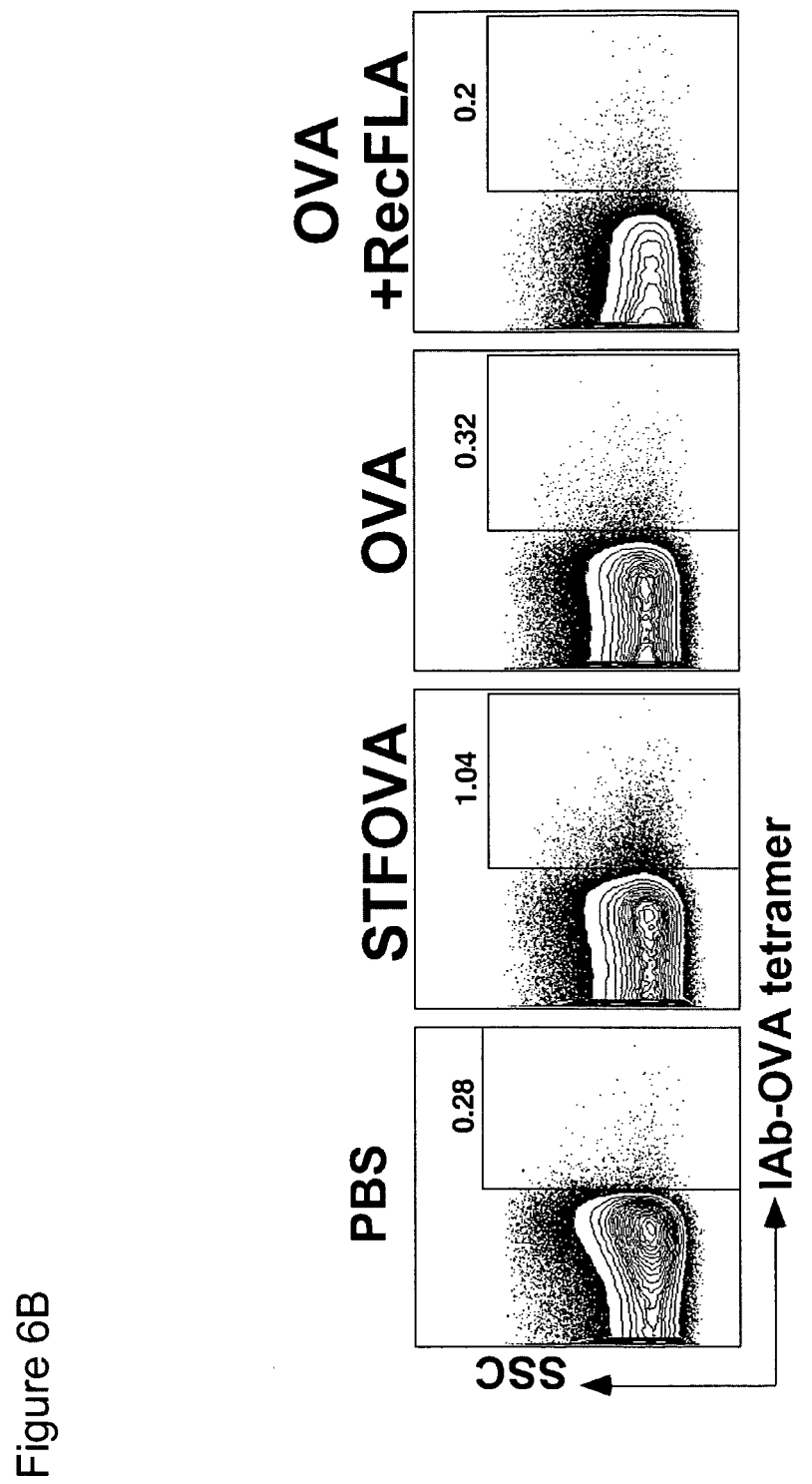
FIG. 6B is a panel of flow cytometry dot plots showing percentages (boxed cells) of endogenous OVA-specific CD4⁺ T cells in tumor draining lymph nodes of vaccinated wt mice (described in FIG. 6A). Cells were stained with an I-A$^b$-OVA tetramer and CD4.

Importantly, this strategy was more efficient than the injection of tumor cells in conjunction with recombinant flagellin (RecFLA) (FIG. 6A) again demonstrating the superior efficacy of linking TLR/NLR ligand to antigens (e.g. tumor associated antigens) versus co-administration (i.e. not physically linked, but administered at the same time or nearly at the same time). Moreover, an endogenous population of CD4+ T cells specific to the tumor-associated antigen could be observed by flow cytometry in mice vaccinated with irradiated EL4-STFOVA (FIG. 6B). Interestingly, this population was not detected in mice vaccinated with irradiated EL4-OVA in conjunction with RecFLA, underlying the importance of the presence of the Flagellin-TAA fusion protein constructs in the tumor cells for an efficient anti-tumor immune response specific for a TAA.

Example 7

Figure 7A:
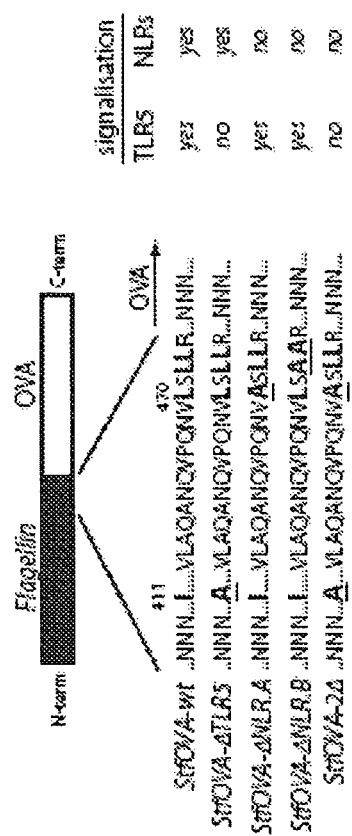
FIG. 7A shows the mutations introduced within the flagellin sequence. Schematic representation of the retroviral plasmid encoding STFOVA. The nucleotide sequence of the C-terminal domain of flagellin is shown and key residues for TLR5 activation (Ile 411) and for Ipaf/Naip5 activation (Leu470, 472, 473) are in bold. These residues were mutated into Alanine (underlined) to impair TLR5 and Ipaf/Naip5 activation, either alone or in combination. Expected effect on TLR5 and NLR activation is shown on the right.
Figure 7B:
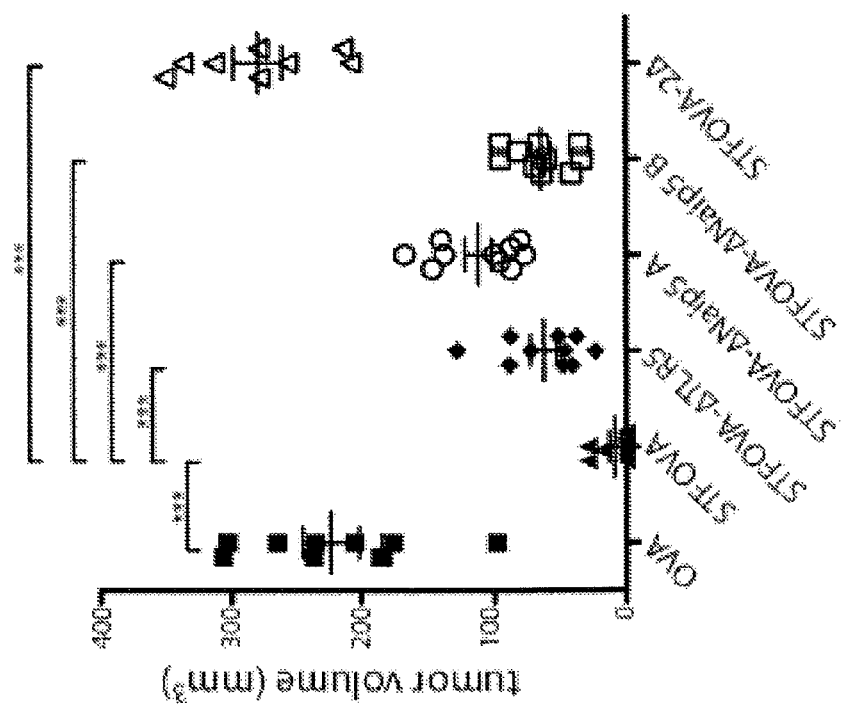
FIG. 7B is a graph showing tumor volume (mm³) in individual wild-type mice injected subcutaneously in the flank with EL4 cells expressing STFOVA or mutated forms of flagellin within the STFOVA fusion (STFOVA-ΔTLR5, STFOVA-ΔNaip5 A, STFOVA-ΔNaip5 B, or STFOVA-2Δ) 20 days after injection. Statistical significance (p value) is indicated on the graph (***p<0.001). Each symbol represents one mouse.
Figure 7C:
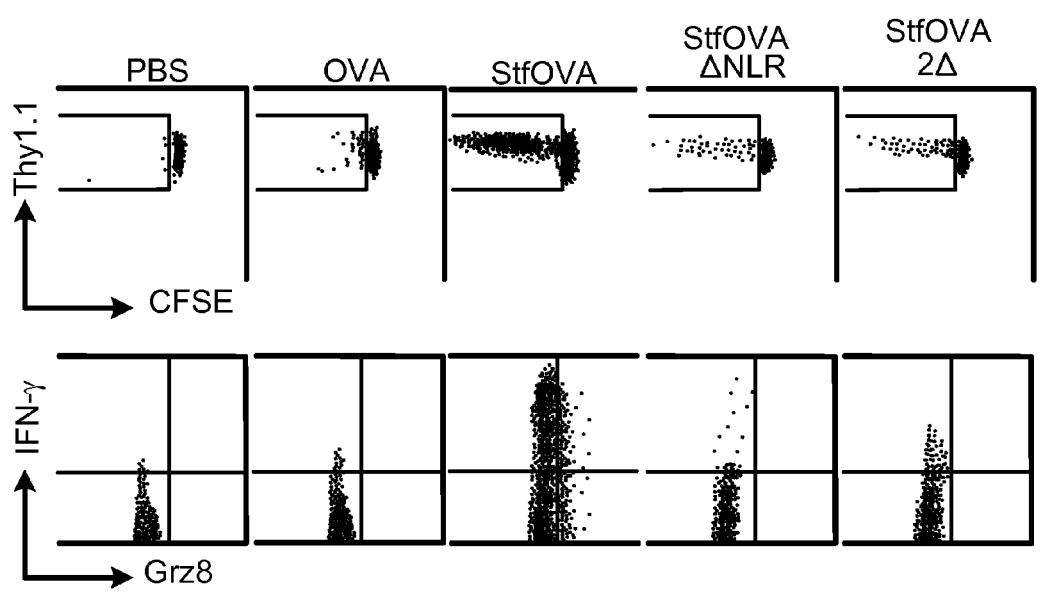
FIG. 7C shows two panels of flow cytometry plots showing proliferation of OVA-specific CD8⁺ OT-I T cells (upper panels) in tumor draining lymph node at day 3 after tumor transplantation of EL4 thymoma expressing OVA, STFOVA or mutated forms of flagellin within the STFOVA fusion protein (STFOVA-ΔNLR, which lacks the NLR Naip5 activating residues, or STFOVA-2Δ which lacks both the TLR5 and NLR Naip5 activating residues). Lower panels shows flow cytometry dot plots showing IFN-γ and granzyme B secretion by OT-I cells from each indicated groups. Cells were stained with Thy1.1 for analysis.

NLR Activating Domain of Flagellin is Required for its Anti-Tumor Potential In Vivo Different EL4-STFOVA cell lines carrying mutations on key residues within flagellin for recognition by TLR5, Ipaf and Naip5 were subcutaneously injected into syngeneic mice. As expected, the mutation of Isoleucine 411 to Alanine (STFOVA-ΔTLR5) (FIG. 7A) restored the capacity of flagellin+ (fusion protein-expressing) cells to form tumor, demonstrating the requirement of TLR5 signaling in flagellin-mediated anti-tumor immunity (FIG. 7B). Single mutation of Leucine L470 (STFOVA-ΔNaip5 A) or the double mutation of Leucine 472/Leucine 473 (STFOVA-ΔNaip5 B) (FIG. 7A), which has been shown to abrogate Naip5 activation [Lightfield, K. L. et al., Critical function for Naip5 in inflammasome activation by a conserved carboxy-terminal domain of flagellin. Nat Immunol 9 (10), 1171 (2008).], also allowed flagellin+ EL4 growth in vivo. Flagellin+ (fusion protein-expressing) tumor cell growth was similar to control cells when flagellin was mutated on both Leucine 470 and Isoleucine 411 (STFOVA-2Δ) to prevent TLR5 and Naip5 activation, respectively (FIG. 7B). Taken together, these results demonstrated that the anti-tumor effect of flagellin fusion protein not only relies on TLR5 activation but also requires NLR (i.e. Ipaf and Naip5) recognition. Taken together, these results demonstrated that the anti-tumor effect of flagellin does not only rely on TLR5 activation but also strongly required NLR (i.e. Naip5 and Ipaf) recognition. In fact, the inability of mutated flagellin to activate NLRs impaired cross-priming of TAA-specific CD8+ T cell as depicted in FIG. 7C showing that flagellin mediated-NLR activation is important for an efficient anti-tumor immune response.

Example 8

Figure 8A:
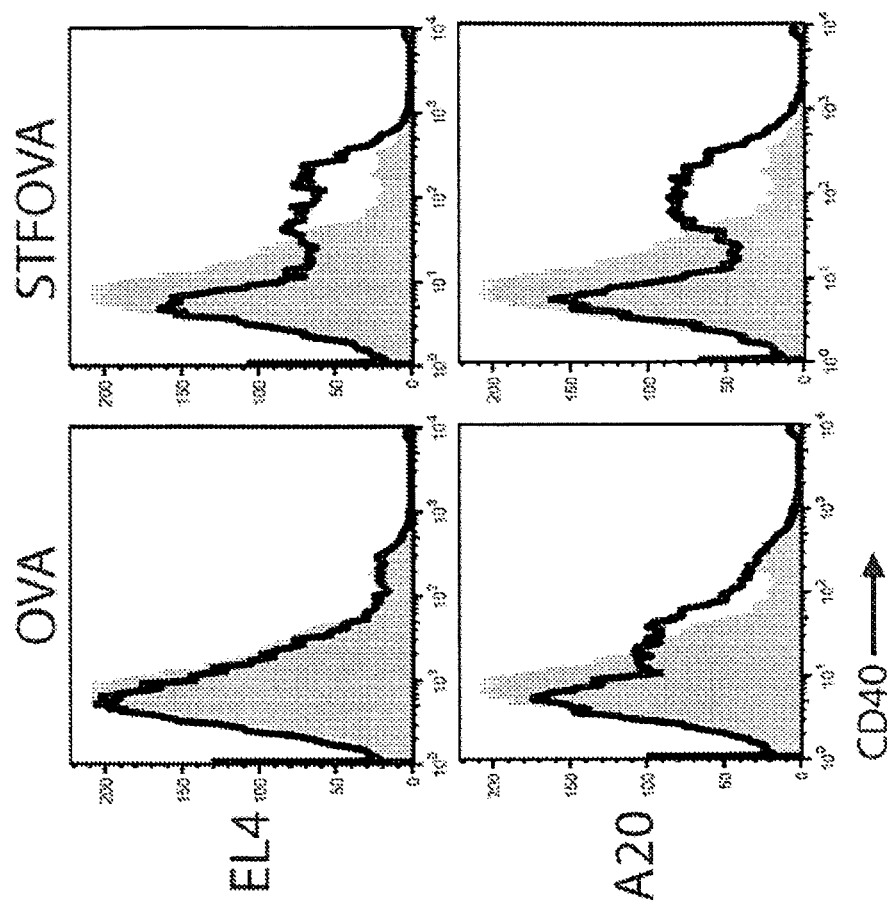
FIG. 8A shows histograms of CD40 expression on splenic dendritic cells after phagocytosis of EL4 or A20 apoptotic tumor cells expressing STFOVA (Flagellin-OVA fusion protein) or OVA (control).
Figure 8B:
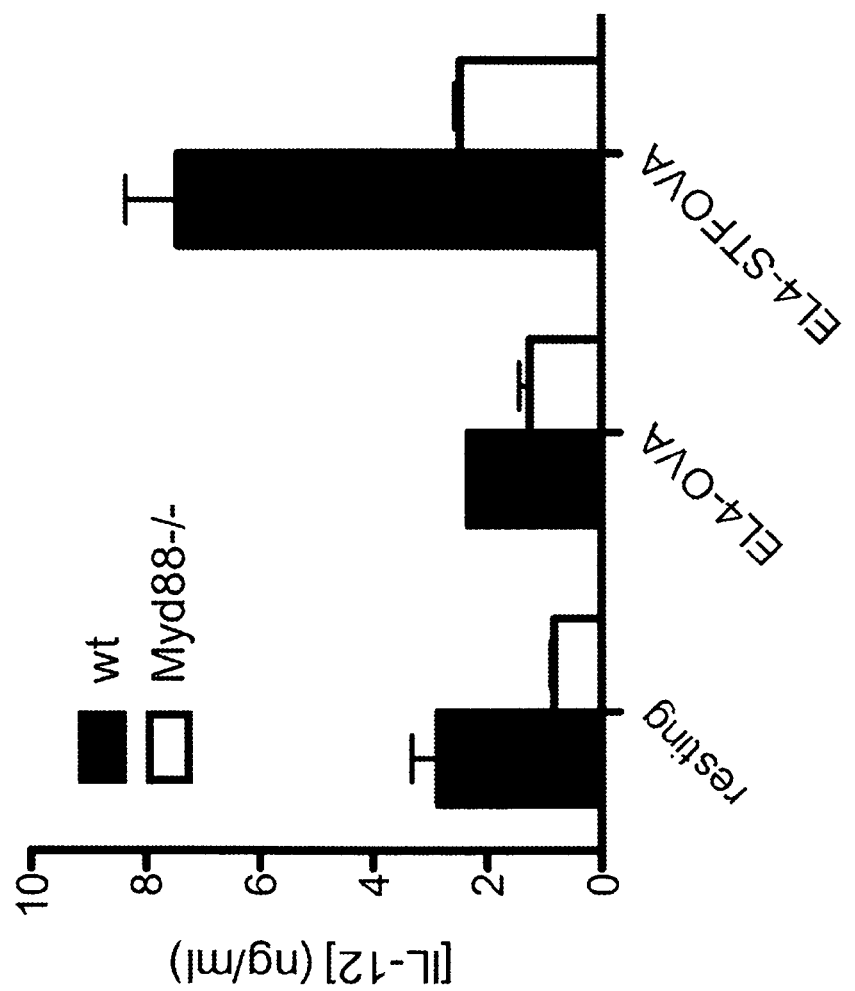

Tumor Cells Expressing a TLR5/Ipaf/Naip5 Ligand Induce Dendritic Cell Activation In vitro studies using dendritic cells (DC) isolated from wild-type (wt) mice show that the phagocytosis of apoptotic tumor cells expressing flagellin fusion protein induce DC maturation as measured by flow cytometry using an antibody specific for the activation marker CD40 (FIG. 8A). Moreover, DC that have phagocytosed STFOVA-expressing apoptotic tumor cells produced the inflammatory cytokine IL-12 in a Myd88 dependent manner (FIG. 8B) confirming that DCs are properly activated after phagocytosis of tumor cells containing the TLR5/Ipaf/Naip5 ligand.

Example 9

Melanoma Cells Expressing a TLR5/Ipaf/Naip5 Ligand Failed to Metastase In Vivo

Thymoma cells EL4 express MHC class 1 molecule and thus can be targeted by CD8+ T cells. In order to demonstrate that tumor cells expressing a low level of MHC molecules can also be rejected in vivo, B16 melanoma cell lines expressing the antigen Eα (the α chain of the MHC class II molecule I-E that is not expressed in C57BL/6 mice) fused or not to flagellin were generated. 100,000 cells were injected alone or in conjunction with 2 ng RecFla (For B16-Eα only; Invivogen, San Diego, Calif.) into the tail vein of wild-type (wt) C57BL/6 recipient mice. 28 days later, lungs were isolated and metastases were observed and numbered under a tissue microscope. As shown in FIG. 9, B16-STF.Eα failed to metastasize in the lung. Moreover, co administration of RecFLA with B16-Eα cells did not impair tumor development. Taken together these results show that tumor cells expressing a low level of MHC molecules were also efficiently eradicated when expressing a fusion flagellin-antigen protein.

Example 10

Immunization with Dendritic Cells Loaded with Tumor Cell Engineered to Express a TLR5/Ipaf/Naip5 Induces Superior Anti-tumor Immune Response Several clinical trials for anti-tumor immunotherapy are based on the use of dendritic cells (DC) loaded with tumor cell extracts. In the present Example, human DC precursors (i.e. circulating monocytes) from tumor bearing patients are isolated and differentiated over night into DCs using a well-defined protocol that involves culture in the cytokines IL-4 and GM-CSF. [Gilliet, M. F. and F. O, Nestle Methods in Mol Med 2001, 10.1385/1-59259-150-7:297; Sallusto, F. and Lanzavecchia, A. (1994). *J. Exp. Med.* 179, 1109-1118; Romani, N., Gruner, S., Brang, D., Kampgen, E., Lenz, A., Trockenbacher, B., Konwalinka, G., Fritsch, P. O., Steinman, R. M., and Schuler, G. (1994) *J. Exp. Med.* 180, 83-93]. DCs are subsequently pulsed for 6 hours with tumor cell extracts (γ-irradiated tumor cell for example) that have been previously engineered to express the TLR5/Ipaf/Naip5 ligand flagellin fused to a tumor associated antigen (e.g. MUC1). Optionally, IFN-γ is added to the culture to increase the maturation of DC prior to injection into the patient. Flagellin-TAA fusion protein expressing-tumor loaded DC is then injected into the patient intravenously or directly into the lymph nodes draining the tumor to ensure the proximity of the DC to T cells in the tumor draining lymph nodes. The number of loaded DC to be injected as well as the frequency of injection is evaluated by several clinical trials. However, suitable numbers of DCs can range, e.g. from about $1 \times 10^6$ to $10 \times 10^7$ cells. Clinical criteria for evaluating of efficacy of immunotherapies are well defined, in particular for solid tumor (J. D Wolchok, A Hoos, S O'day, J. S Weber, O Hamid, C Lebbe, M Maio, M Binder, O Bohnsack, G Nichol, R Humphrey, F. S Hodi. Clinical Cancer Research, 2009 vol. 15 (23) pp. 7412-7420). Evaluation of the efficacy of this DC-based therapy may follow these criteria.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

While the compositions and methods of this invention have been described in terms of specific embodiments, it will be apparent to those of skill in the art that variations may be applied to the compositions and methods and in the steps or in the sequence of steps of the method described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention as defined by the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A composition comprising a dendritic cell (DC), wherein said DC has internalized a tumor cell expressing a fusion protein, said fusion protein comprising:
   a flagellin or fragment thereof and a tumor-associated antigen (TAA),
   wherein the flagellin or fragment thereof is capable of binding to one or more of Toll-like receptor-5 (TLR5), Naip5 or Ipaf.

2. A method for treating a cancer in a patient in need of such treatment comprising administering to said patient the composition of claim 1 in an effective amount for eliciting an anti-tumor immune response.

3. A method for treating a cancer in a patient in need of such treatment comprising administering to said patient a composition comprising a tumor cell expressing a fusion protein, wherein said fusion protein comprises:
   a flagellin or fragment thereof and a tumor associated antigen (TAA), in an effective amount for eliciting an anti-tumor immune response,
   wherein the flagellin or fragment thereof is capable of binding to one or more of Toll-like receptor-5 (TLR5), Naip5 or Ipaf.

4. The method of claim 2, wherein said DC has phagocytosed said tumor cell.

5. The method of claim 3, wherein said patient is a human.

6. The method of claim 2, wherein said tumor cell is an autologous cell.

7. The method of claim 2, wherein said DC is an autologous cell.

8. The method of claim 2, wherein said tumor cell is lethally irradiated.

9. The method of claim 2, wherein said patient is a human.

10. The method of claim 3, wherein said tumor cell is an autologous cell.

11. The method of claim 3, wherein said tumor cell is lethally irradiated.

12. The method of claim 1, wherein the flagellin comprises an amino acid sequence substantially identical to an amino acid sequence selected from the group consisting of SEQ NOs: 1, 3, 4, 5, 6, 7, 8, 9, 10, 11, 12, 13, 14, 15, 16, 17, 18, 19 and 20, or a fragment thereof.

13. The method of claim 1, wherein the flagellin fragment comprises and an amino acid sequence at least 80% identical to the amino acid sequence of SEQ ID NO: 31 or SEQ ID NO: 32.

14. The method of claim 3, wherein the flagellin comprises an amino acid sequence substantially identical to an amino acid sequence selected from the group consisting of SEQ NOs: 1, 3, 4, 5, 6, 7, 8, 9, 10, 11, 12, 13, 14, 15, 16, 17, 18, 19 and 20, or a fragment thereof.

15. The method of claim 3, wherein the flagellin fragment comprises and an amino acid sequence at least 80% identical to the amino acid sequence of SEQ ID NO: 31 or SEQ ID NO: 32.

* * * * *